US009801727B2

(12) United States Patent
Ferro et al.

(10) Patent No.: US 9,801,727 B2
(45) Date of Patent: Oct. 31, 2017

(54) TIBIAL BASE PLATE AND METHOD FOR ATTACHING A TIBIAL BASE PLATE ON A TIBIA

(71) Applicant: AOD Holdings, LLC, Arroyo Grande, CA (US)

(72) Inventors: Thomas D. Ferro, Arroyo Grande, CA (US); Donald Lee, Arroyo Grande, CA (US); John Parks, Arroyo Grande, CA (US); Austin T. Ferro, Arroyo Grande, CA (US)

(73) Assignee: AOD Holdings, LLC, Arroyo Grande, CA (US)

( * ) Notice: Subject to any disclaimer, the term of this patent is extended or adjusted under 35 U.S.C. 154(b) by 0 days.

(21) Appl. No.: 14/530,822

(22) Filed: Nov. 2, 2014

(65) Prior Publication Data

US 2015/0342742 A1     Dec. 3, 2015

Related U.S. Application Data

(60) Provisional application No. 62/003,957, filed on May 28, 2014, provisional application No. 62/045,411, filed on Sep. 3, 2014.

(51) Int. Cl.
| *A61F 2/38* | (2006.01) |
| *A61B 17/15* | (2006.01) |
| *A61F 2/30* | (2006.01) |
| *A61B 17/16* | (2006.01) |
| *A61B 90/00* | (2016.01) |

(52) U.S. Cl.
CPC ............ *A61F 2/389* (2013.01); *A61B 17/157* (2013.01); *A61B 17/1604* (2013.01); *A61B 2090/0801* (2016.02); *A61F 2002/30688* (2013.01); *A61F 2002/30878* (2013.01)

(58) Field of Classification Search
CPC ...................................... A61F 2/389
See application file for complete search history.

(56) References Cited

U.S. PATENT DOCUMENTS

| 2011/0190898 A1* | 8/2011 | Lenz ......................... A61F 2/38 623/20.32 |
| 2013/0173010 A1* | 7/2013 | Irwin ......................... A61F 2/38 623/20.32 |

\* cited by examiner

*Primary Examiner* — Christopher D Prone
*Assistant Examiner* — Suba Ganesan
(74) *Attorney, Agent, or Firm* — McDonnell Boehnen Hulbert & Berghoff LLP

(57) ABSTRACT

A tibial base plate for attaching to a resected surface at a proximal end of a tibia is provided. The tibial base plate includes a bridge, a pair of compartments and a stem. The bridge has a first contact surface sitting on the resected surface. The compartments are disposed at opposite sides of the bridge and extend in an anterior-posterior direction to form a notch to accommodate a tibial eminence. Each of the compartments has a second contact surface sitting on the resected surface. The stem is connected to the bridge and the compartments and inset into the proximal end of the tibia. The stem has an outer surface. The outer surface is canted towards the notch as insetting into the proximal end of the tibia. The stem is engaged with a cutting slot on the resected surface into the proximal end of the tibia.

11 Claims, 32 Drawing Sheets

TIBIAL BASE PLATE AND METHOD FOR ATTACHING A TIBIAL BASE PLATE ON A TIBIA

RELATED APPLICATIONS

This application claims priority to U.S. provisional Application Nos. 62/003,957 filed May 28, 2014 and 62/045,411 filed Sep. 3, 2014, which are herein incorporated by reference.

BACKGROUND

Technical Field

The present disclosure relates to tibial base plates. More particularly, the present disclosure relates to tibial base plates for bi-cruciate sparing orthopedic knee implants in total knee arthroplasty (TKA) procedures.

Description of Related Art

Orthopedic prosthesis include a femoral component that attaches to the distal end of the femur, along with a tibial base plate that attaches to the proximal end of the resected tibia, and an intermediate tibial bearing component that attached to the tibial base plate. The tibial bearing component is used as an intermediate surface to reduce friction and create the needed contact surface area for correct flexion and extension movement.

Generally speaking, the tibial base plate must initially be sized to fit in proportion to the resected cut of the proximal tibial end. Moreover, it must also be sized in correlation with the femoral component to promote proper articulation. A common issue with current bi-cruciate sparing base plate design is that the resection makes the tibial eminence susceptible to avulsion. Current methods have been to have a vertical cut from the anterior to the anterior cruciate ligament (ACL) insertion point. Afterwards, secondary operations would attempt to round out the anterior portion using a file or clippers that can jeopardize the integrity of the tibial eminence.

In addition to protecting the tibial eminence, the surgeon is responsible for proper cutting of the tibia to assure that the tibial eminence is well protected and the tibial base plate does not overhang on the anterior portion of the tibia. The surgeon must also assure that the stem of the tibial base plate is properly placed, in order to create a seamless flow on the anterior portion from the baseplate to the tibia, making sure the integrity of the tibial eminence is not compromised. However, both the risks of tibial eminence avulsion and anterior overhang are prevalent today.

SUMMARY

A technical aspect of the present disclosure is to provide a tibial base plate which allows bi-cruciate sparing orthopedic knee implant in a total knee arthroplasty (TKA) procedure.

According to an embodiment of the present disclosure, a tibial base plate for attaching to a resected surface at a proximal end of a tibia in a total knee arthroplasty (TKA) procedure is provided. The tibial base plate includes a bridge, a pair of compartments and a stem. The bridge has a first contact surface sitting on the resected surface. The compartments are disposed at opposite sides of the bridge and extend in an anterior-posterior direction away from the bridge to form a notch to accommodate a tibial eminence of the tibia, in which each of the compartments has a second contact surface sitting on the resected surface. The stem is connected to the bridge and the compartments and inset into the proximal end of the tibia. The stem has an outer surface facing away from the notch, in which the outer surface is canted in the anterior-posterior direction towards the notch as insetting into the proximal end of the tibia. The stem is engaged with a cutting slot on the resected surface into the proximal end of the tibia.

In one or more embodiments of the present disclosure, the tibial base plate has an inner surface flush with the notch and is at least partially located on the bridge, the compartments and the stem. The inner surface is angled such that the notch diverges as insetting into the proximal end of the tibia.

In one or more embodiments of the present disclosure, the tibial base plate further includes a pair of pegs. The pegs are respectively disposed on the second contact surfaces, in which each of the pegs is engaged with a peg hole on the resected surface.

In one or more embodiments of the present disclosure, the pegs are canted and substantially parallel with the outer surface.

In one or more embodiments of the present disclosure, the compartments are symmetric.

In one or more embodiments of the present disclosure, the compartments are asymmetric.

Another technical aspect of the present disclosure is to provide a method for attaching a tibial base plate on a tibia, which allows bi-cruciate sparing orthopedic knee implant in a total knee arthroplasty (TKA) procedure.

According to an embodiment of the present disclosure, a method for attaching a tibial base plate on a tibia is provided. A tibia cut guide includes at least one first rail inclined at a first angle relative to a longitudinal direction along the tibia. The method includes the following steps (it is appreciated that the sequence of the steps and the sub-steps as mentioned below, unless otherwise specified, can all be adjusted upon the actual needs, or even executed at the same time or partially at the same time):

(1) Fixing a tibia cut guide to an anterior portion of the tibia.

(2) Engaging slidably a tibial stem punch and guard with the first rail of the tibia cut guide such that the tibial stem punch and guard moves linearly to and away from the tibia along the first rail.

(3) Punching the tibial stem punch and guard into the tibia at the first angle to act as a barrier guarding a tibial eminence of the tibia and to form a cutting slot at the tibia.

(4) Making a resected surface on the tibia by a blade passing through a blade slot of the tibia cut guide at a region outside the tibial eminence as guarded by the tibial stem punch and guard.

(5) Fixing the tibial base plate on the resected surface by engaging a stem of the tibial base plate with the cutting slot and a tibial eminence of the tibia being accommodated in a notch of the tibial base plate.

In one or more embodiments of the present disclosure, the method further includes the following step:

(6) Coring peg holes on the resected surface such that the peg holes are canted and substantially parallel with an outer surface of the stem facing away from the notch.

In one or more embodiments of the present disclosure, an extra medullary (EM) rod includes a height adjustment knob for fastening an intermediate component to the EM rod. The step (1) includes the following sub-steps:

(1.1) Mounting the extra medullary (EM) rod to the tibia.

(1.2) Attaching the intermediate component to the EM rod.

(1.3) Connecting the tibia cut guide to the intermediate component.

(1.4) Finding a height of the tibia cut guide relative to the tibia.

(1.5) Fastening the height adjustment knob of the EM rod to fasten the intermediate component to the EM rod to maintain the height found.

In one or more embodiments of the present disclosure, the step (1) includes the following sub-steps:

(1.1) Mounting an extra medullary (EM) rod to the tibia.

(1.2) Attaching the intermediate component to the EM rod.

(1.3) Connecting the tibia cut guide to the intermediate component.

(1.6) Finding a second angle of the tibia cut guide relative to an anterior-posterior direction of the tibia to guard the tibial eminence and fixing the tibia cut guide relative to the tibia based on the second angle found.

In one or more embodiments of the present disclosure, the step (1.6) includes the following sub-steps:

(1.6.1) Engaging slidably a first visual reference (VR) guide with the first rail of the tibia cut guide such that the first VR guide moves linearly to and away from the tibia along the first rail.

(1.6.2) Adjusting the tibia cut guide to find the second angle of the first VR guide relative to the anterior-posterior direction to guard the tibial eminence.

In one or more embodiments of the present disclosure, the intermediate component includes a first external rotation guide and a second external rotation guide. The first external rotation guide is connected with the tibia cut guide and the second external rotation guide is attached to the EM rod. The second external rotation guide includes a second rail such that the first external rotation guide can slide along the second rail relative to the second external rotation guide. The first external rotation guide includes an engaging pin connected with a release button and the second external rotation guide includes a plurality of teeth. An engagement is formed between the engaging pin and the teeth. The step (1.6.2) includes the following sub-steps:

(1.6.2.1) Pressing on the release button to release the engagement between the engaging pin and the teeth, so as to allow the first external rotation guide to slide along the second rail relative to the second external rotation guide to find the second angle.

(1.6.2.2) Releasing the release button to make the engagement between the engaging pin and the teeth to fix the position of the first external rotation guide relative to the second external rotation guide after the second angle is found.

In one or more embodiments of the present disclosure, the intermediate component includes a first external rotation guide and a second external rotation guide. The first external rotation guide is connected with the tibia cut guide and the second external rotation guide is attached to the EM rod. The second external rotation guide includes a second rail such that the first external rotation guide can slide along the second rail relative to the second external rotation guide. The second external rotation guide has a channel at a side along a sliding direction. The first external rotation guide includes a sliding button and a locking pin. The sliding button passes through a sliding slot of the first external rotation guide. The locking pin secures the sliding button to the first external rotation guide and mates with a slot of the first external rotation guide. The slot curves towards the channel at one end and away from the channel at the other end, such that the sliding button presses on a compression surface of the channel and the relative position of the first external rotation guide and the second external rotation guide is fixed by friction when the sliding button is at a first position of the sliding slot. The sliding button leaves the compression surface when the sliding button is at a second position of the sliding slot opposite to the first position. The step (1.6.2) includes the following sub-steps:

(1.6.2.3) Moving the sliding button to the second position to leave the sliding button from the compression surface, so as to allow the first external rotation guide to slide along the second rail relative to the second external rotation guide to find the second angle.

(1.6.2.4) Moving the sliding button to the first position to press the sliding button on the compression surface to fix the position of the first external rotation guide relative to the second external rotation guide after the second angle is found.

In one or more embodiments of the present disclosure, the intermediate component includes a first external rotation guide and a second external rotation guide. The first external rotation guide is connected with the tibia cut guide and engages with the second external rotation guide. The first external rotation guide includes a rotary structure such that the tibia cut guide can rotate about itself relative to the first external rotation guide. The tibia cut guide further includes a hex nut. The step (1.6.2) includes the following sub-steps:

(1.6.2.5) Rotating the tibia cut guide about itself relative to the first external rotation guide.

(1.6.2.6) Fastening the hex nut to fix the tibia cut guide relative to the first external rotation guide after the second angle is found.

In one or more embodiments of the present disclosure, a second visual reference (VR) guide has a plurality of markers, the step (1) includes the following sub-steps:

(1.1) Mounting the extra medullary (EM) rod to the tibia.

(1.2) Attaching the intermediate component to the EM rod.

(1.3) Connecting the tibia cut guide to the intermediate component.

(1.7) Moving the second VR guide with the markers along an anterior-posterior direction of the tibia through the blade slot of the tibia cut guide until a referencing edge of the second VR guide touches the anterior portion of the tibia, so as to find an anterior-posterior length for the tibial stem punch and guard.

In one or more embodiments of the present disclosure, the intermediate component includes a first external rotation guide and a second external rotation guide. The first external rotation guide is connected with the tibia cut guide and the second external rotation guide is attached to the EM rod. The second external rotation guide includes a second rail such that the first external rotation guide can slide along the second rail relative to the second external rotation guide. The tibia cut guide has a blade slot and at least a speed pin hole communicated with a locking hole inside the first external rotation guide. The step (1) includes the following sub-steps:

(1.1) Mounting the extra medullary (EM) rod to the tibia.

(1.2) Attaching the intermediate component to the EM rod.

(1.3) Connecting the tibia cut guide to the intermediate component.

(1.8) Measuring a medial lateral (ML) width of the tibia by a ML sizing stylus engaged with the blade slot of the tibia cut guide.

(1.9) Inserting a speed pin into the speed pin hole of the tibia cut guide and the locking hole inside the first external rotation guide to fix the position of the tibia cut guide relative to the first external rotation guide after the ML width is found.

In one or more embodiments of the present disclosure, a medial lateral (ML) centering device includes a pair of arms and a button. The pair of arms is located adjacent to the tibia and a bottom surface of each of the arms is at the same plane/level as a bottom surface of the blade slot of the tibia cut guide. The ML centering device includes a spring and a central gear. The spring is attached to one of the arms. The central gear drives the pair of arms. The button is directly connected to one of the arms, such that the arm connected with the button is opened when the button is pushed, driving the other arm to open through an action of the central gear. The arms return to closed positions when the button is released. The ML centering device includes a pair of forks located above the tibia. The ML centering device further includes a tab extending in the same direction as the pair of forks. The tab is used to insert into the blade slot of the tibia cut guide. The step (1) includes the following sub-steps:

(1.1) Mounting the extra medullary (EM) rod to the tibia.

(1.2) Attaching the intermediate component to the EM rod.

(1.3) Connecting the tibia cut guide to the intermediate component.

(1.10) Centering the tibia cut guide relative to the medial lateral (ML) width and the location of the tibial eminence by an adjustment through the push and release of the button of the ML centering device such that bi-cruciate ligaments are centered within the pair of forks of the ML centering device.

According to another embodiment of the present disclosure, a method for attaching a tibial base plate on a tibia is provided. A tibia cut guide includes at least one first rail inclined at a first angle relative to a longitudinal direction along the tibia. At least one punch is engaged to the tibia cut guide and the tibia. The method includes the following steps (it is appreciated that the sequence of the steps and the sub-steps as mentioned below, unless otherwise specified, can all be adjusted upon the actual needs, or even executed at the same time or partially at the same time):

(1) Fixing a tibia cut guide to an anterior portion of the tibia.

(7) Engaging slidably the punch with the first rail of the tibia cut guide such that the punch moves linearly to and away from the tibia along the first rail.

(8) Resecting a medial and lateral plateau.

(9) Impacting the punch into the tibia at the first angle to act as a barrier guarding a tibial eminence of the tibia and to form a cutting slot at the tibia.

(4) Making a resected surface on the tibia by a blade passing through a blade slot of the tibia cut guide at a region outside the tibial eminence as guarded by the punch.

(5) Fixing the tibial base plate on the resected surface by engaging a stem of the tibial base plate with the cutting slot and a tibial eminence of the tibia being accommodated in a notch of the tibial base plate.

In one or more embodiments of the present disclosure, the punch includes an upper part and a lower part. The method further includes the following step:

(10) Calibrating the position of the upper part relative to the lower part in an anterior-posterior (AP) direction.

In one or more embodiments of the present disclosure, an anterior-posterior (AP) adjustment/calibration guide is connected to an intermediate component connecting the tibia cut guide to the tibia. The AP adjustment/calibration guide includes a pair of connection rods and a turning knob. Each of the connection rods connects a punch fixation base of the punch to the turning knob in a way that a rotation of the turning knob drives a movement of the connection rods and the punch fixation bases along an anterior-posterior direction. The method includes the following step:

(11) Calibrating the position of the punch relative to the tibia in an anterior-posterior (AP) direction.

When compared with the prior art, the embodiments of the present disclosure mentioned above have at least the following advantages:

(1) In the embodiments of the present disclosure, the pair of the compartments of the tibial base plate forms a notch to accommodate the tibial eminence of the tibia. In this way, a bi-cruciate sparing orthopedic knee implant for the tibial portion of a total knee arthroplasty (TKA) procedure is allowed.

(2) In the embodiments of the present disclosure, the stem of the tibial base plate can be fitly engaged with the cutting slot on the resected surface into the proximal end of the tibia. In this way, the tibial base plate can be stably fixed to the resected surface.

(3) In the embodiments of the present disclosure, the bridge has a first contact surface sitting on the resected surface. In this way, the chance of anterior overhang is reduced.

(4) In the embodiments of the present disclosure, the inner surface of the tibial base plate flush with the notch is angled such that the notch diverges as insetting into the proximal end of the tibia. In this way, the tibial eminence is allowed to have a wider base and the chance of tibial avulsion is reduced.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
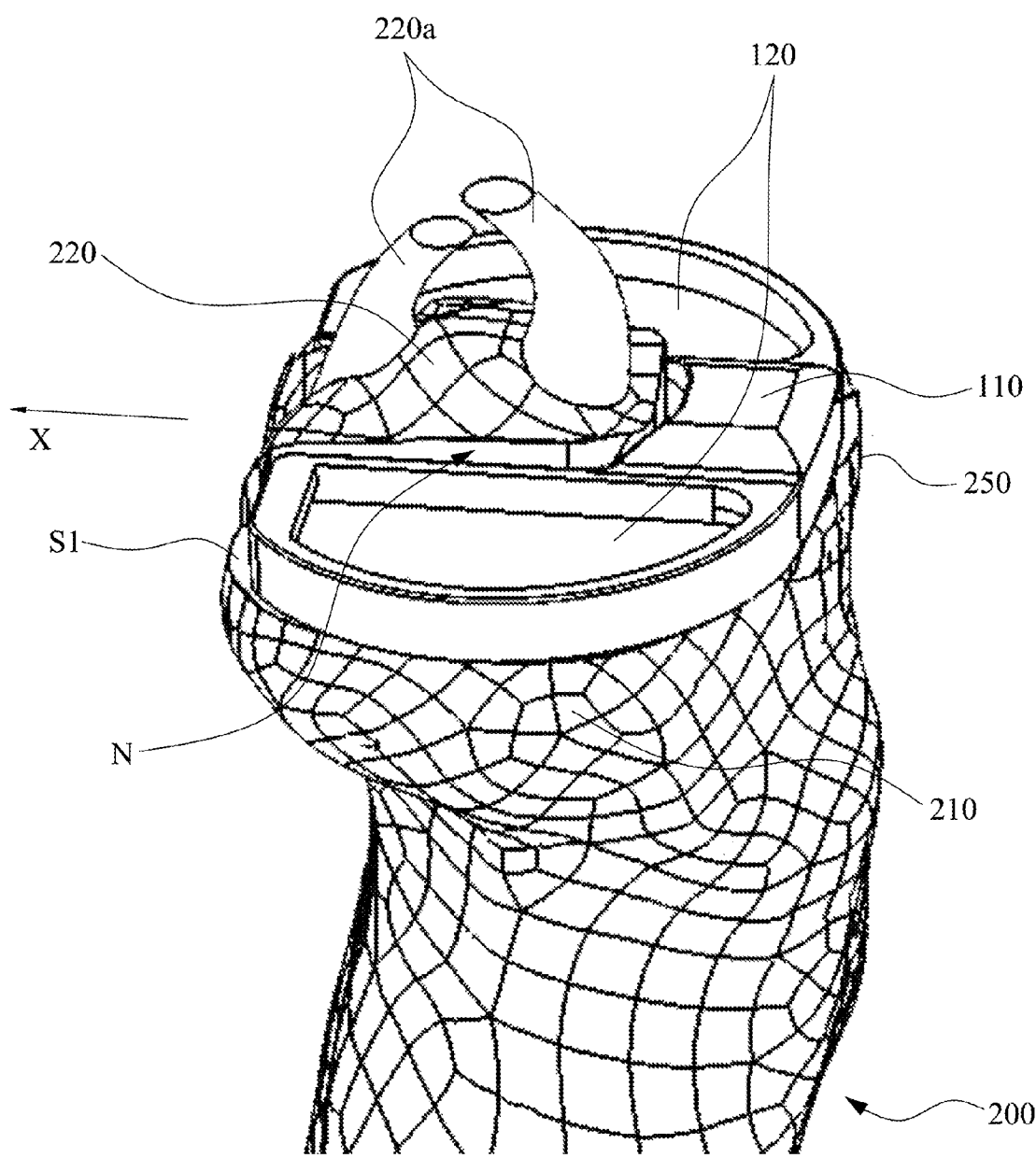
FIG. 1 is a perspective view of a tibial base plate according to an embodiment of the present disclosure, in which the tibial base plate is attached to a resected surface at a proximal end of a tibia.

Drawings will be used below to disclose a plurality of embodiments of the present disclosure. For the sake of clear illustration, many practical details will be explained together in the description below. However, it is appreciated that the practical details should not be used to limit the claimed scope. In other words, in some embodiments of the present disclosure, the practical details are not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 is a perspective view of a tibial base plate 100 according to an embodiment of the present disclosure, in which the tibial base plate 100 is attached to a resected surface S1 at a proximal end 210 of a tibia 200. As shown in FIG. 1, the tibial base plate 100 for attaching to the resected surface S1 at the proximal end 210 of the tibia 200 in a total knee arthroplasty (TKA) procedure is provided. The tibial base plate 100 includes a bridge 110, a pair of compartments 120 and a stem 130. The bridge 110 has a first contact surface S2 sitting on the resected surface S1. In this way, the chance of anterior overhang is reduced. The compartments 120 are disposed at opposite sides of the bridge 110 and extend in an anterior-posterior direction X away from the bridge 110 to form a notch N to accommodate a tibial eminence 220 of the tibia 200, in which each of the compartments 120 has a second contact surface S3 sitting on the resected surface S1. The stem 130 is connected to the bridge 110 and the compartments 120, and inset into the proximal end 210 of the tibia 200. The stem 130 has an outer surface S4 facing away from the notch N, in which the outer surface S4 is canted in the anterior-posterior direction X towards the notch N as insetting into the proximal end 210 of the tibia 200. The stem 130 is engaged with a cutting slot (not shown in FIG. 1) on the resected surface S1 into the proximal end 210 of the tibia 200.

Figure 2:
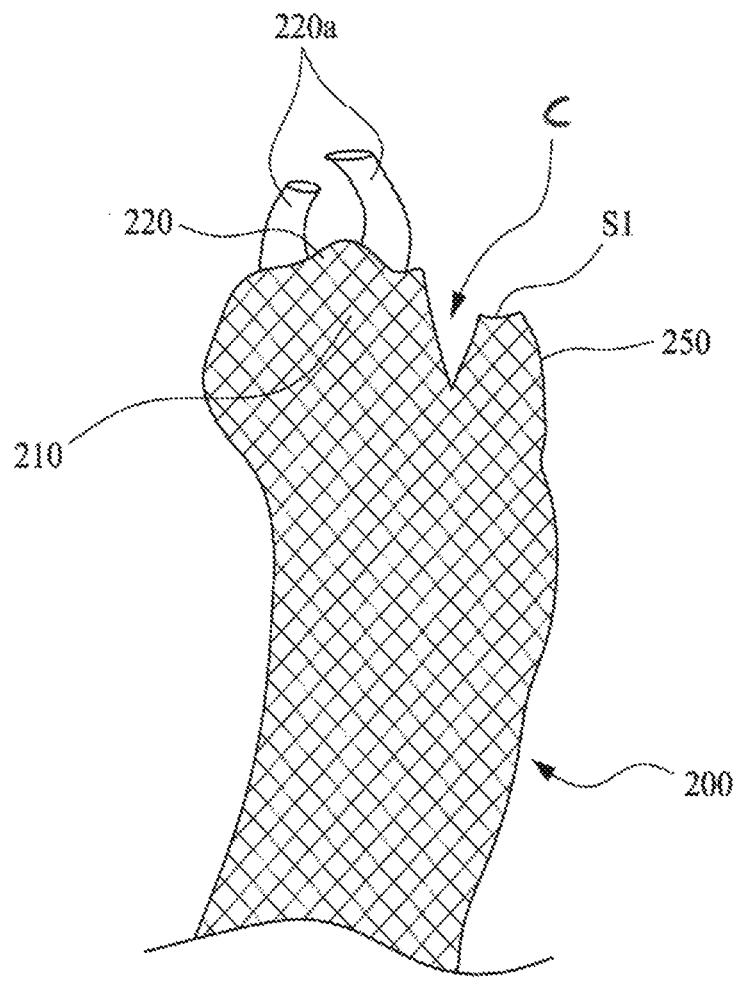
FIG. 2 is a cross sectional view of the tibia with a cutting slot ready for attaching the tibial base plate of FIG. 1.

FIG. 2 is a cross sectional view of the tibia 200 with a cutting slot C ready for attaching the tibial base plate 100 of FIG. 1. As shown in FIG. 2, the cutting slot C is located on the resected surface S1 into the proximal end 210 of the tibia 200. In addition, the cutting slot C allows the tibial eminence 220 to have a wider base in the direction of the tibial eminence 220 extending towards into the cutting slot C.

As shown in FIG. 1, in this embodiment, the notch N is deep enough to accommodate the bi-cruciate ligaments 220a (i.e., the anterior cruciate ligament and the posterior cruciate ligament). As a result, a bi-cruciate sparing orthopedic knee implant for the tibial portion of a total knee arthroplasty (TKA) procedure is allowed.

Figure 3:
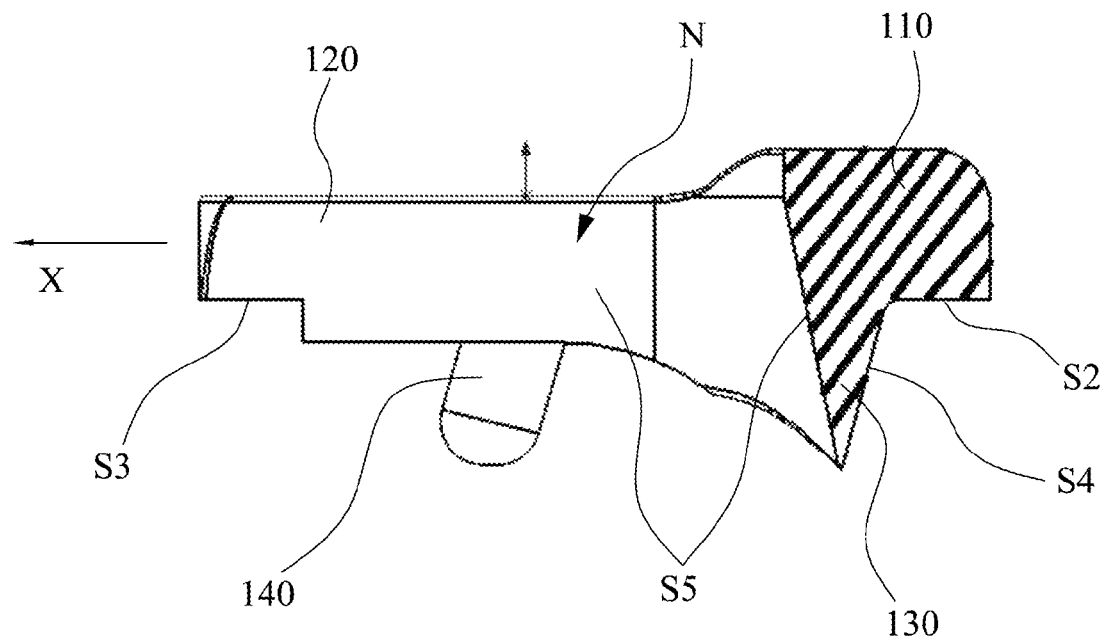
FIG. 3 is a sectional view of the tibial base plate of FIG. 1.
Figure 4:
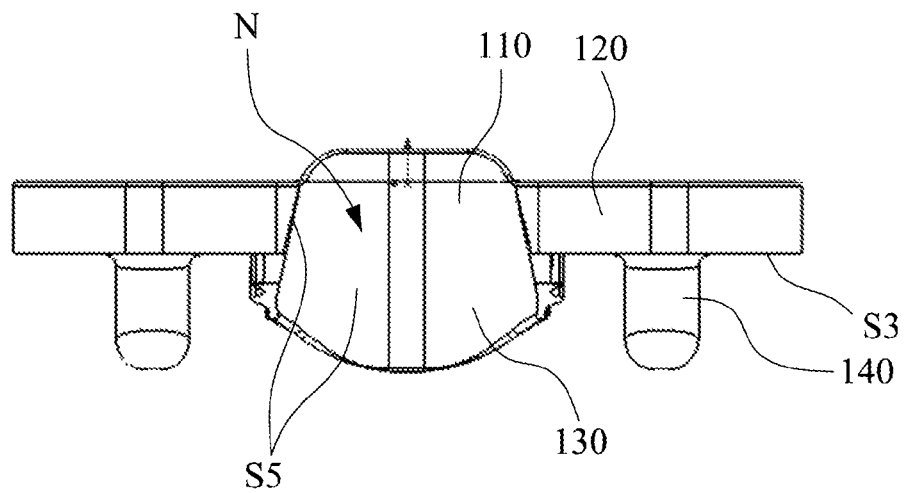
FIG. 4 is a back view (as viewed from a posterior direction) of the tibial base plate of FIG. 1.

FIG. 3 is a sectional view of the tibial base plate 100 of FIG. 1. FIG. 4 is a back view (as viewed from a posterior direction) of the tibial base plate 100 of FIG. 1. As shown in FIGS. 3-4, the tibial base plate 100 has an inner surface S5 flush with the notch N and is at least partially located on the bridge 110, the compartments 120 and the stem 130. The inner surface S5 is angled such that the notch N diverges as insetting into the proximal end 210 of the tibia 200. In this way, the tibial eminence 220 is allowed to have a wider base as described above. This angled wider base of the tibial eminence 220 will discourage the avulsion of the tibial bone block when the knee is in high strain and the anterior cruciate ligament (ACL) is applying a tensile force onto the tibial eminence 220. In other words, the chance of tibial avulsion is reduced.

In addition, to be more specific, the geometry and dimensions of the stem 130 is in direct correlation with that of a tibial stem punch and guard (not shown in FIGS. 1-4) used to create the cutting slot C (shown in FIG. 2) on the resected surface S1 into the proximal end 210 of the tibia 200. Therefore, the stem 130 can be fitly engaged with the cutting slot C created by the tibial stem punch and guard. In this way, the tibial base plate 100 can be stably fixed to the resected surface S1.

As shown in FIGS. 3-4, the tibial base plate 100 further includes a pair of pegs 140 respectively disposed on the second contact surfaces S3, in which each of the pegs 140 is engaged with a peg hole (not shown in FIGS. 3-4) on the resected surface S1. Therefore, the attachment of the tibial base plate 100 on the resected surface S1 is further secured.

In addition, the pegs 140 are canted and substantially parallel with the outer surface S4. This allows for an angled linear entry of the tibial base plate 100 onto the resected surface S1 during operation to avoid clearance issue.

In this embodiment, the compartments 120 are symmetric. However, this does not intend to limit the present disclosure. In other embodiments, the compartments 120 can be designed as asymmetric, depending on the actual need.

Another technical aspect of the present disclosure provides a method for attaching the tibial base plate 100 on the tibia 200, which allows bi-cruciate sparing orthopedic knee implant in a total knee arthroplasty (TKA) procedure.

Figure 5:
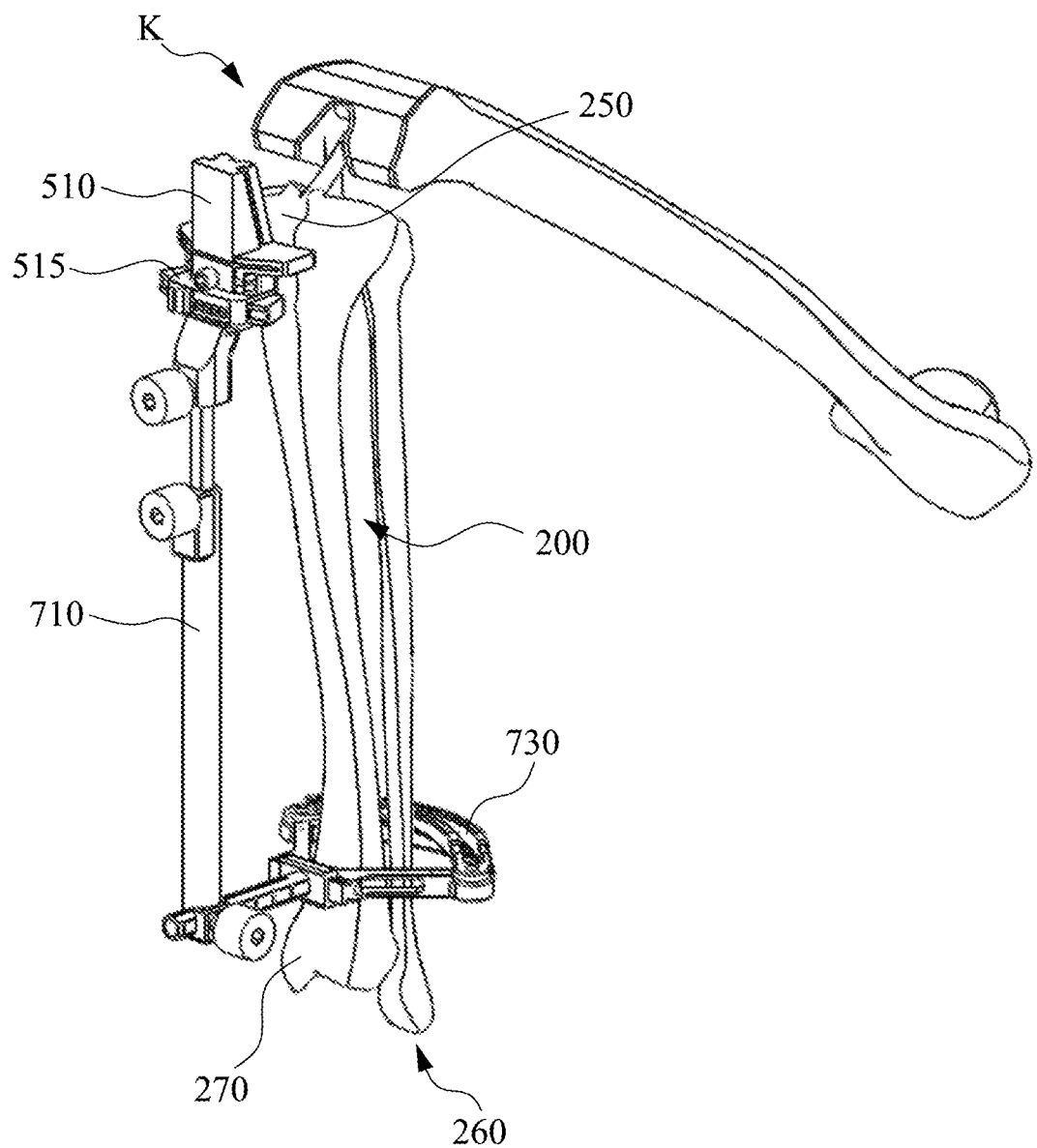
FIG. 5 is a general assembly showing a tibia cut guide fixed to the anterior portion of the tibia.

FIG. 5 is a general assembly showing a tibia cut guide 510 fixed to the anterior portion 250 of the tibia 200. In details, as shown in FIG. 5, the knee K is flexed to improve the exposure of the proximal end 210 of the tibia 200. The spring-loaded ankle clamp 730 is then placed just above the malleoli 270 of the ankle 260. Attached to the ankle clamp 730 is an extra medullary (EM) rod 710 with an intermediate component 515 attached to the other end of the EM rod 710. Moreover, a tibia cut guide 510 is connected to the intermediate component 515 and fixed to the anterior portion 250 of the tibia 200. The tibia cut guide 510 is then lined up parallel with the tibia 200 when viewing from a frontal plane. An angle between the tibia cut guide 510 and the tibia 200 when viewing from a sagittal plane can be adjusted by the surgeon.

Figure 6:
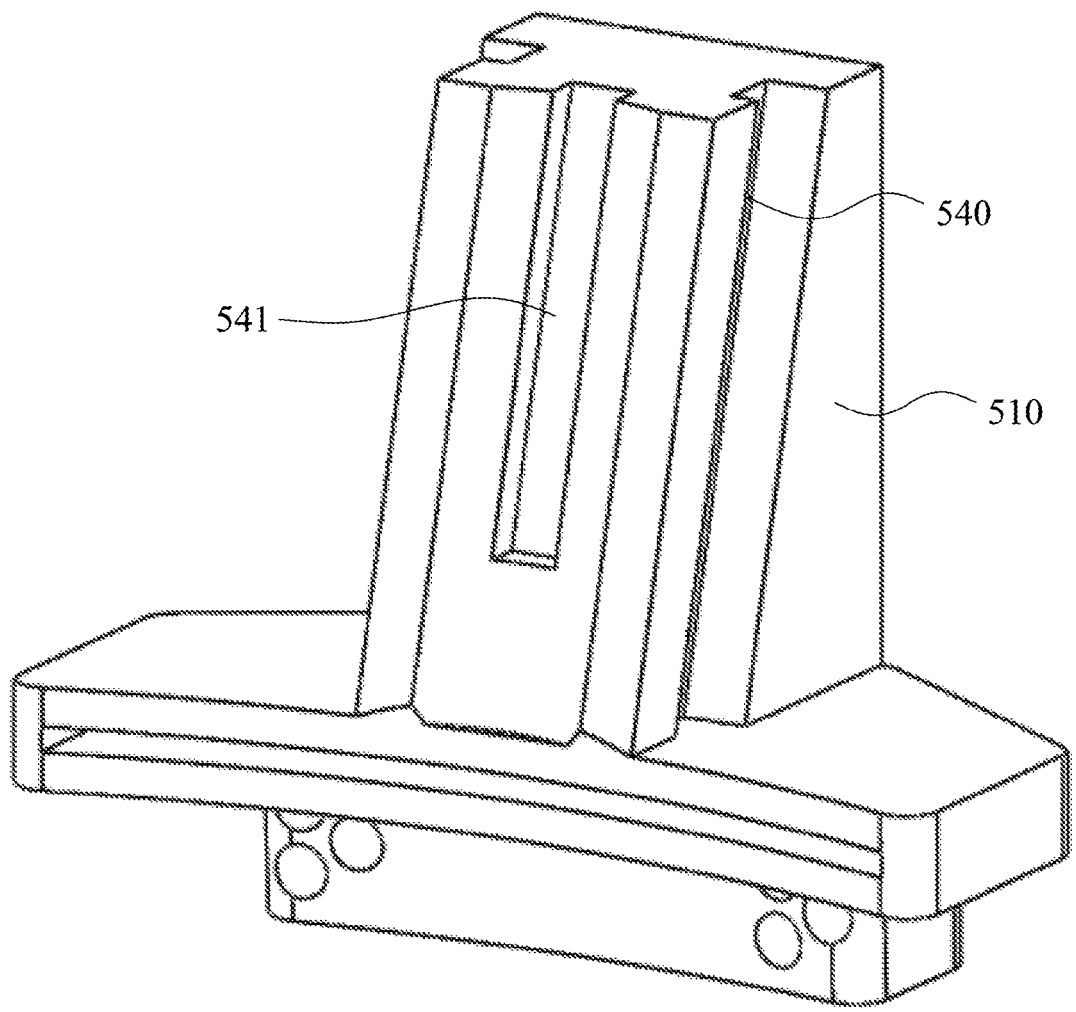
FIG. 6 is a perspective view of the tibia cut guide of FIG. 5.

FIG. 6 is a perspective view of the tibia cut guide 510 of FIG. 5. As shown in FIG. 6, the tibia cut guide 510 features a vertically extending feature that has an angled first rail 540 and a stopper rail 541.

Figure 7:
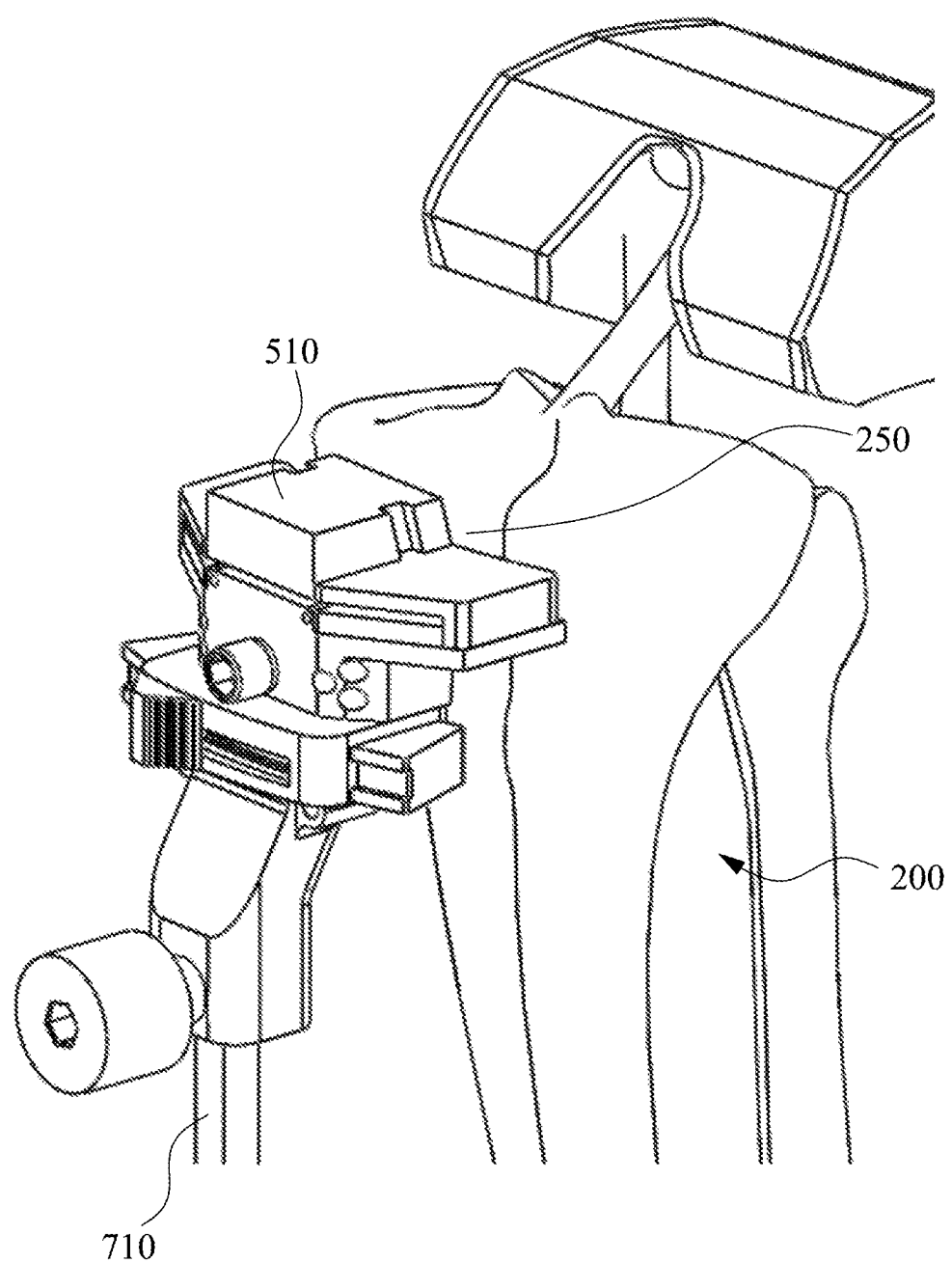
FIG. 7 is a general assembly showing another tibia cut guide fixed to the anterior portion of the tibia.
Figure 8:
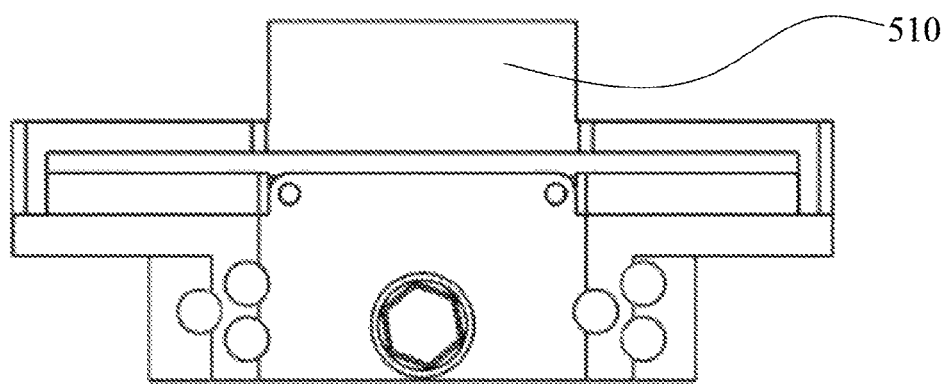
FIG. 8 is a front view of the tibia cut guide of FIG. 7.
Figure 9:
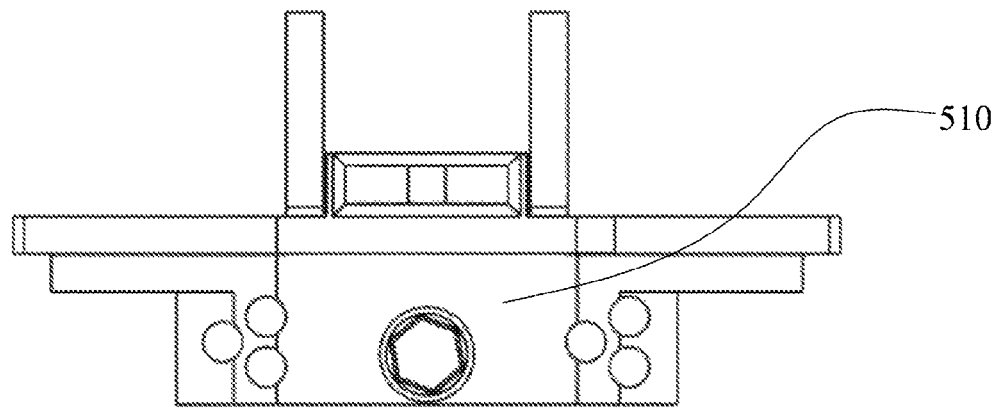
FIG. 9 is a front view of the tibia cut guide of FIG. 7 functioning in one configuration.
Figure 10:
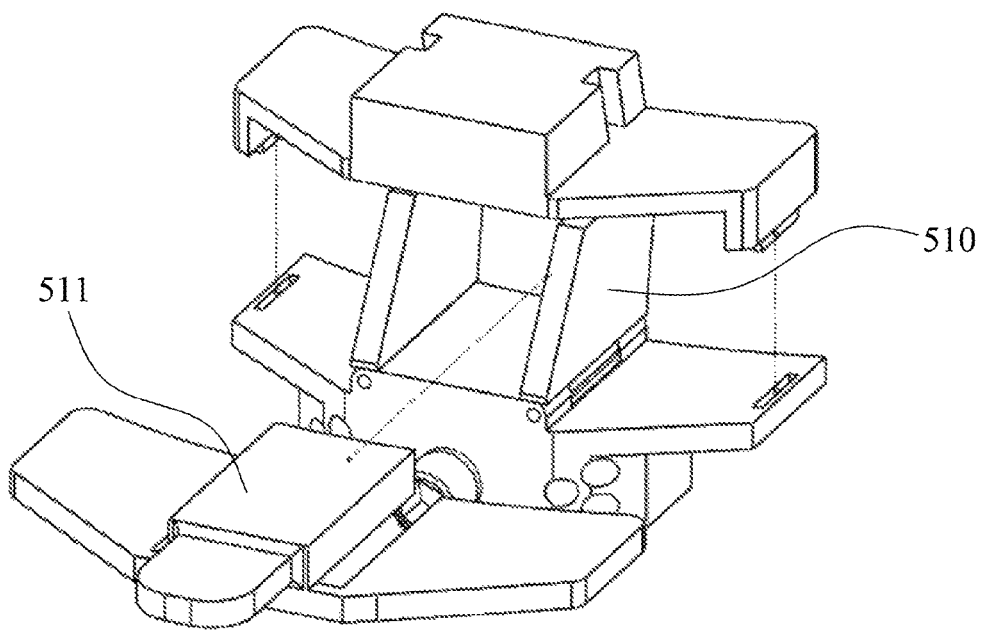
FIG. 10 is a perspective view of the tibia cut guide of FIG. 7 functioning in another configuration.

FIG. 7 is a general assembly showing another tibia cut guide 510 fixed to the anterior portion 250 of the tibia 200. FIG. 8 is a front view of the tibia cut guide 510 of FIG. 7. In FIGS. 7-8, the tibia cut guide 510 is a modular structure that can function in two different configurations for a sagittal cut as well as a planar cut. FIG. 9 is a front view of the tibia cut guide 510 of FIG. 7 functioning in one configuration. As shown in FIG. 9, the tibia cut guide 510 functions for the first sagittal cut. FIG. 10 is a perspective view of the tibia cut guide 510 of FIG. 7 functioning in another configuration. As shown in FIG. 10, a module piece 511 is attached to the tibia cut guide 510 for the function of making the planar cut.

Figure 11:
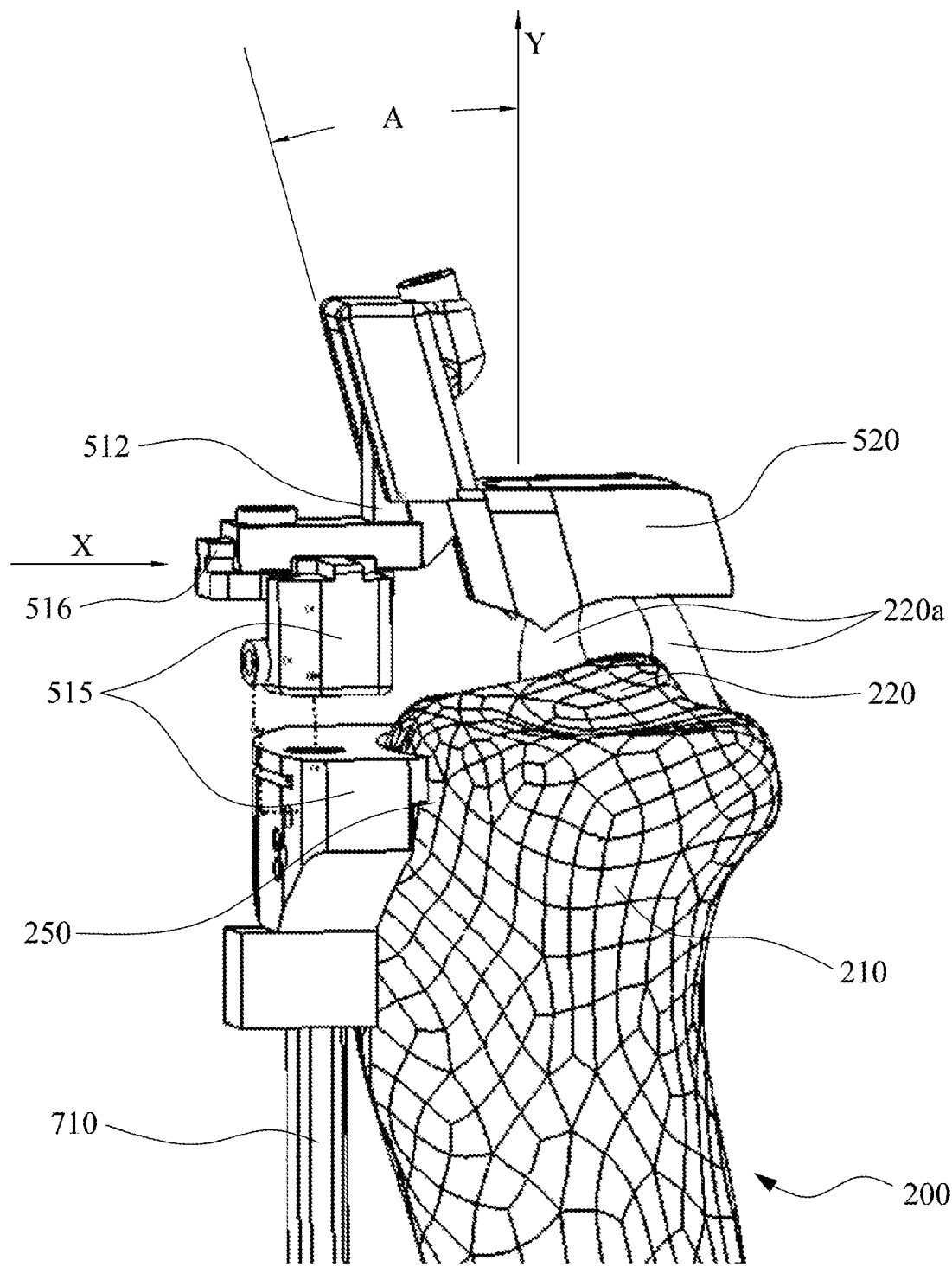
FIG. 11 is a perspective view showing a procedure to attach the tibial base plate on the tibia, in which a tibial stem punch and guard to be punched into the proximal end of the tibia.
Figure 12:
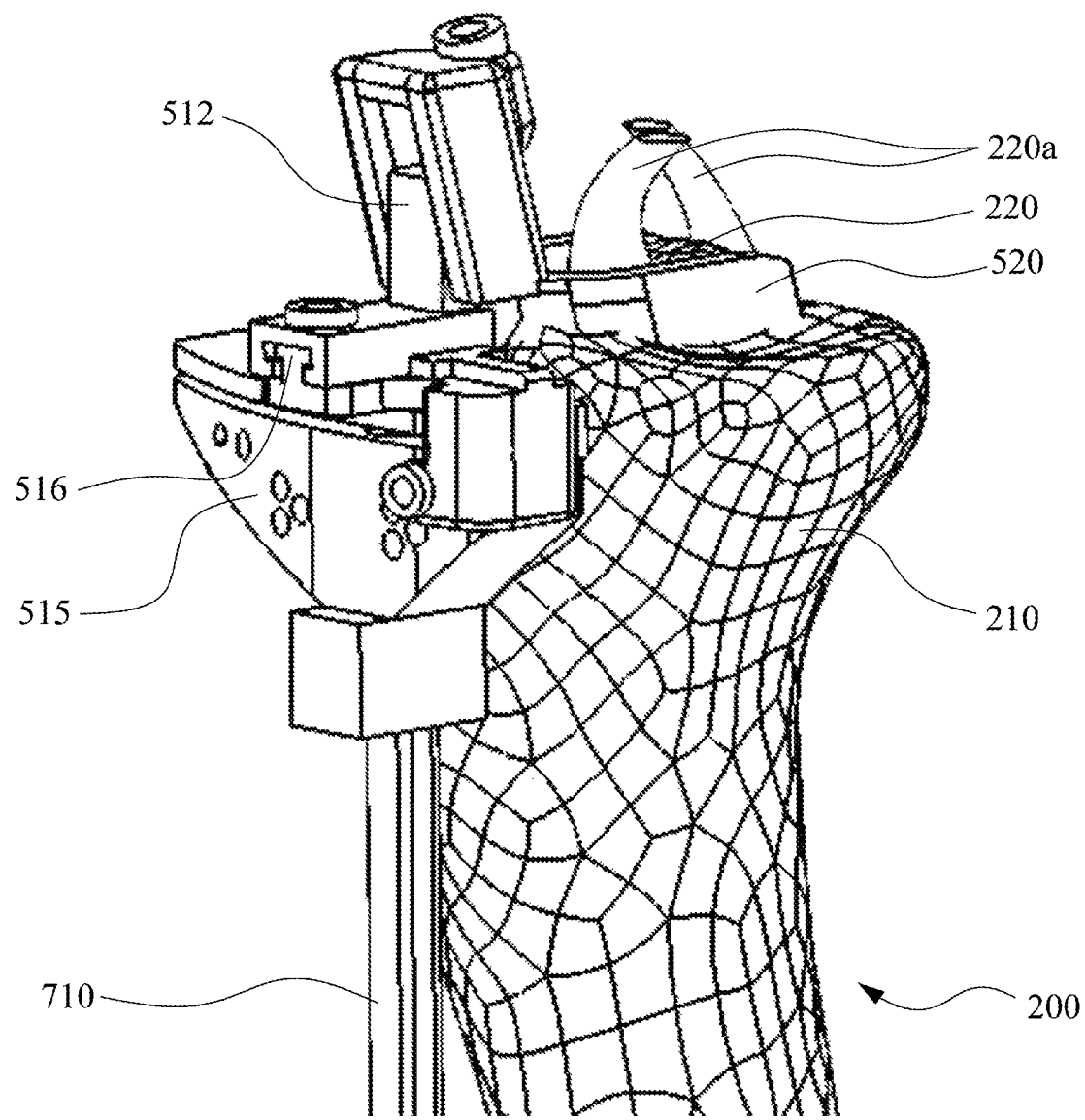
FIG. 12 is a perspective view showing the tibial stem punch and guard being punched into the tibia.

FIG. 11 is a perspective view showing a procedure to attach the tibial base plate 100 on the tibia 200, in which a tibial stem punch and guard 520 to be punched into the proximal end 210 of the tibia 200. FIG. 12 is a perspective view showing the tibial stem punch and guard 520 being punched into the tibia 200. As shown in FIGS. 11-12, the tibial stem punch and guard 520 is slidably connected to an angled rail component 512 at a first angle A relative to a longitudinal direction Y along the tibia 200. In addition, an anterior-posterior (AP) adjustment guide 516 is attached to the intermediate component 515. The AP adjustment guide 516 allows the angled rail component 512 together with the tibial stem punch and guard 520 to slide along the anterior-posterior direction X relative to the tibia 200.

Figure 13:
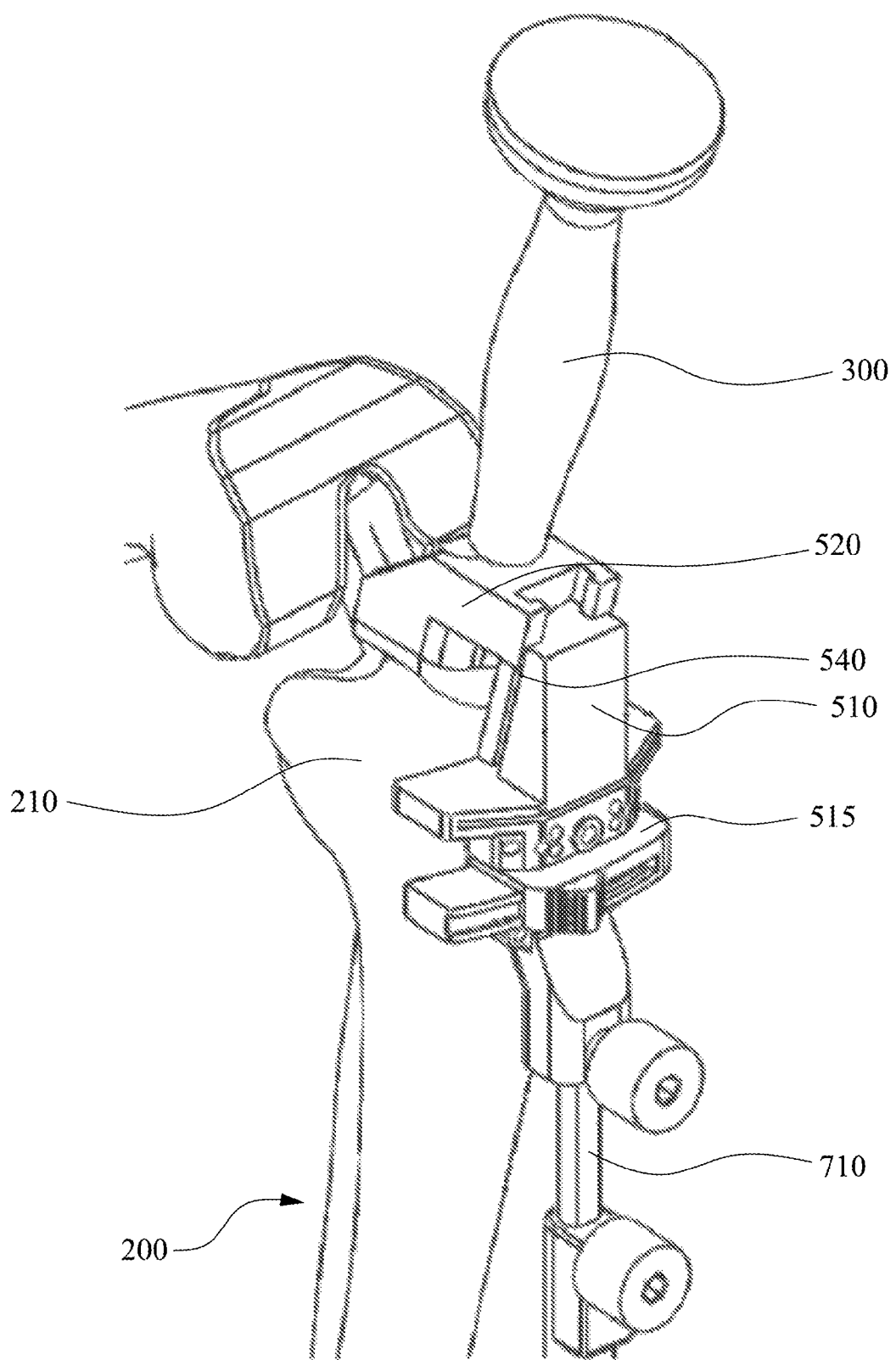
FIG. 13 is a perspective view of the tibial stem punch and guard engaged with the tibia cut guide and attached with an impactor.

FIG. 13 is a perspective view of the tibial stem punch and guard 520 engaged with the tibia cut guide 510 and attached with an impactor 300. In practical applications, as shown in FIG. 13, for example, the tibial stem punch and guard 520 can be driven into the tibia 200 using a device such as a slap hammer (not shown) or the impactor 300. The impactor 300 engages with the tibial stem punch and guard 520 by mating with the top of the tibial stem punch and guard 520 with a threaded hole or other means of engaging. However, this mode of punching the tibial stem punch and guard 520 into the tibia 200 does not intend to limit the present disclosure.

In summary, the method for attaching the tibial base plate 100 on the tibia 200 includes the following steps (it is appreciated that the sequence of the steps and the sub-steps as mentioned below, unless otherwise specified, can all be adjusted upon the actual needs, or even executed at the same time or partially at the same time):

(1) Fixing the tibia cut guide 510 to the anterior portion 250 of the tibia 200.

(2) Engaging slidably the tibial stem punch and guard 520 with the first rail 540 of the tibia cut guide 510 such that the tibial stem punch and guard 520 moves linearly to and away from the tibia 200 along the first rail 540. As mentioned above, the first rail 540 is inclined at the first angle A relative to a longitudinal direction Y along the tibia 200. This angled entry of the tibial stem punch and guard 520 to engage with the tibia cut guide 510 can help to avoid clearance issue.

(3) Punching the tibial stem punch and guard 520 into the tibia 200 at the first angle A to act as a barrier guarding a tibial eminence 220 of the tibia 200 and to form a cutting slot C (shown in FIG. 2) at the tibia 200. That means, before the resected surface S1 is made in the next step, the tibial eminence 220 is already well guarded and protected. As mentioned above, the tibial stem punch and guard 520 can be punched into the tibia 200 by using a slap hammer or the impactor 300. However, this does not intend to limit the present disclosure.

Figure 14:
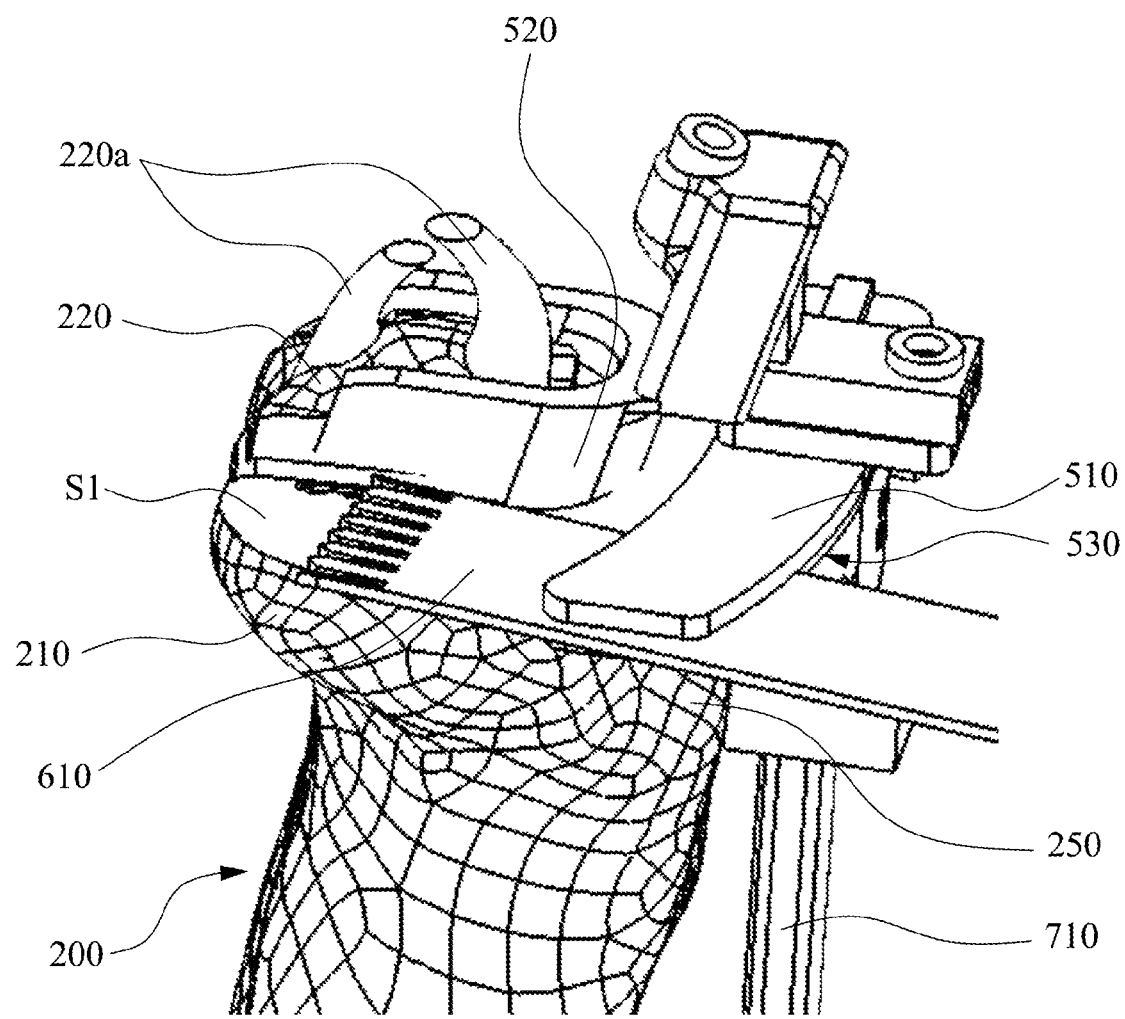
FIG. 14 is a perspective view showing the usage of the blade for making a resected surface on the tibia.

(4) Making a resected surface S1 on the tibia 200 by a blade 610 passing through a blade slot 530 of the tibia cut guide 510 at a region outside the tibial eminence 220 as guarded by the tibial stem punch and guard 520. In this way, the tibial eminence 220 is well protected and will not be damaged when the resected surface S1 is made. FIG. 14 is a perspective view showing the usage of the blade 610 for making the resected surface S1 on the tibia 200. In other words, as shown in FIG. 14, the resected surface S1 is made on the tibia 200 before the tibial base plate 100 (not shown in FIG. 14) is attached on the tibia 200. In addition, since the blade slot 530 is remained open, the resection of the anterior portion of the tibia 200 can be made without having intermediate steps to readjust the tibia cut guide 510 or other components to aid in the resection, while the tibial stem punch and guard 520 still acts as a guard to protect the tibial eminence 220.

(5) Fixing the tibial base plate 100 on the resected surface S1 by engaging the stem 130 of the tibial base plate 100 with the cutting slot C (shown in FIG. 2) and the tibial eminence 220 of the tibia 200 being accommodated in a notch N of the tibial base plate 100. Please refer to FIG. 1 for the tibial base plate 100 being attached to the resected surface S1 at the proximal end 210 of the tibia 200.

In this embodiment, the tibia cut guide 510 is asymmetric. However, this does not intend to limit the present disclosure. In other embodiments, the tibia cut guide 510 can be designed as symmetric, depending on the actual need.

Figure 15:
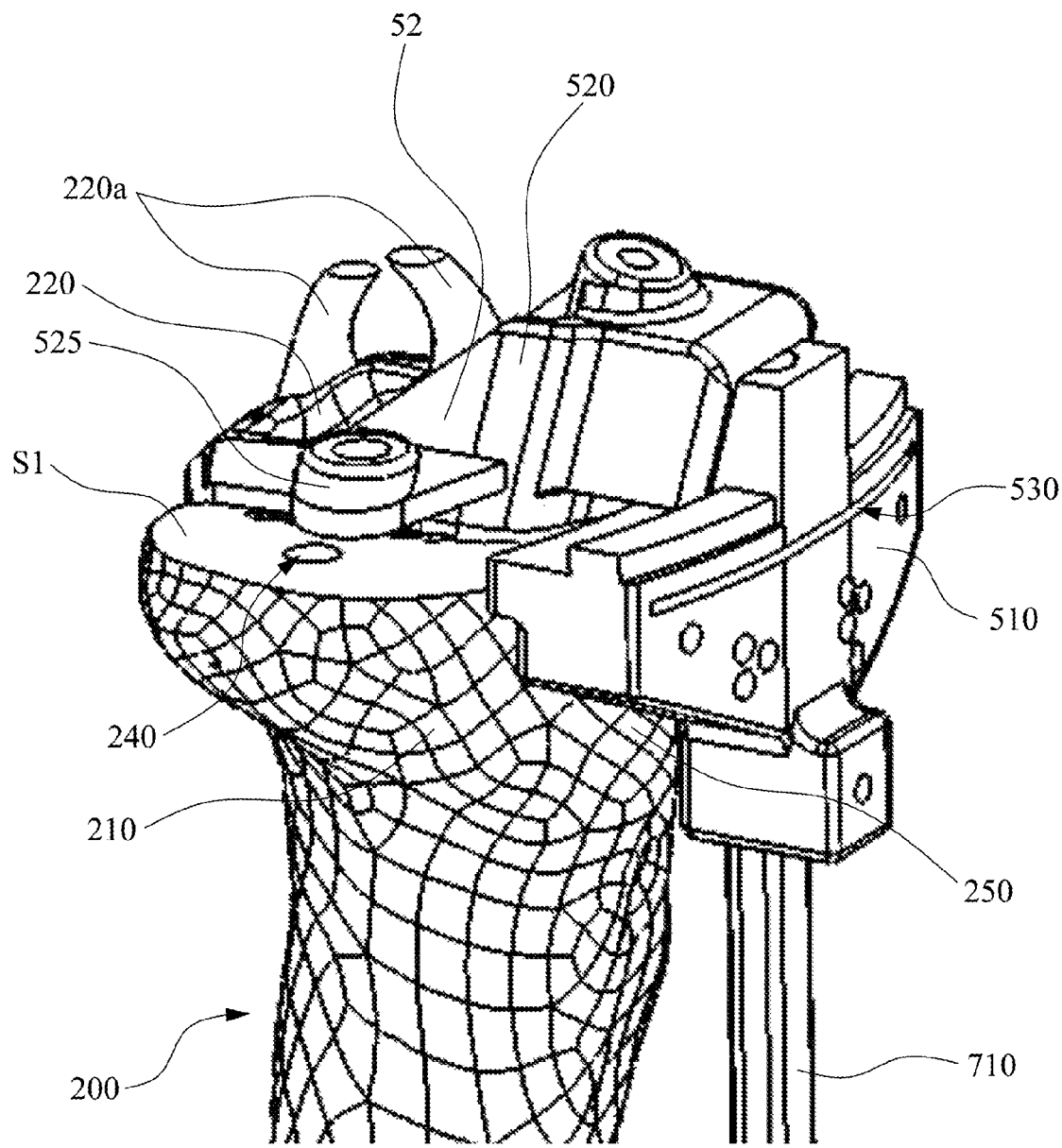
FIG. 15 is a perspective view showing a procedure to attach the tibial base plate on the tibia, in which a peg hole is cored on the resected surface on the tibia.

FIG. 15 is a perspective view showing a procedure to attach the tibial base plate 100 on the tibia 200, in which a peg hole 240 is cored on the resected surface S1 on the tibia 200. To be specific, as shown in FIG. 15, the method for attaching the tibial base plate 100 on the tibia 200 further includes the following step:

(6) Coring peg holes 240 on the resected surface S1 such that the peg holes 240 are canted and substantially parallel with an outer surface S4 of the stem 130 facing away from the notch N. Similar as aforementioned, this orientation of the peg holes 240 facilitates the angled linear entry of the tibial base plate 100 onto the resected surface S1 during operation to avoid clearance issue.

Structurally speaking, as shown in FIG. 15, the tibial stem punch and guard 520 can have coring guides 525 on the medial and lateral sides to allow for the peg holes 240 to be cored out of the tibia 200. In this embodiment, the depth and the width from the center of the peg holes 240 can be identical for both the medial and lateral sides.

Figure 16:
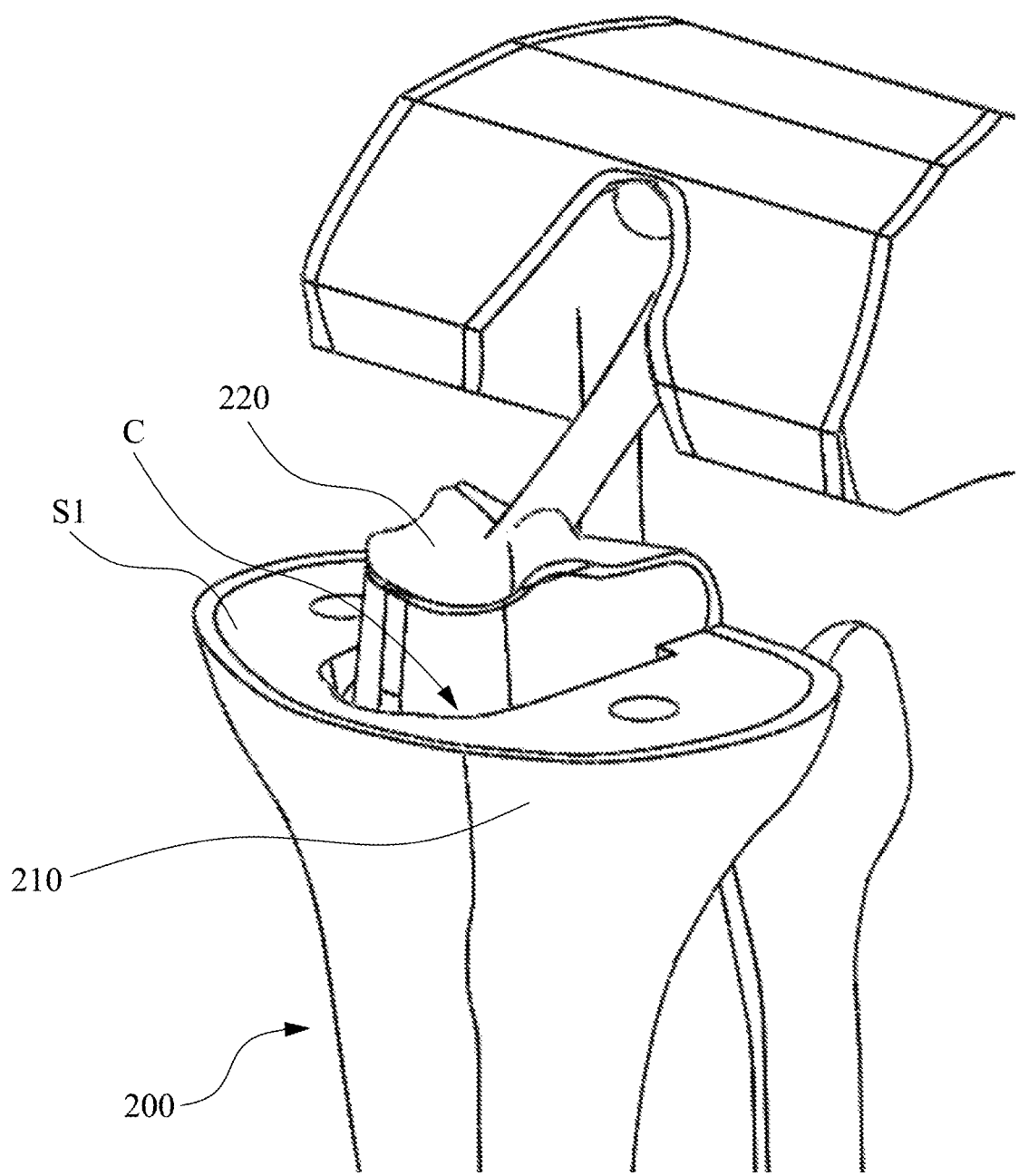
FIG. 16 is a perspective view showing the resected surface completely formed at the proximal end of the tibia.

FIG. 16 is a perspective view showing the resected surface S1 completely formed at the proximal end 210 of the tibia 200. As shown in FIG. 16, the cutting slot C is formed on the resected surface S1 and located around the tibial eminence 220. The shape of the cutting slot C refers to the features of the tibial stem punch and guard 520 as mentioned above. Furthermore, the cutting slot C is used as a cavity that the stem 130 of the tibial base plate 100 can engage.

Figure 17:
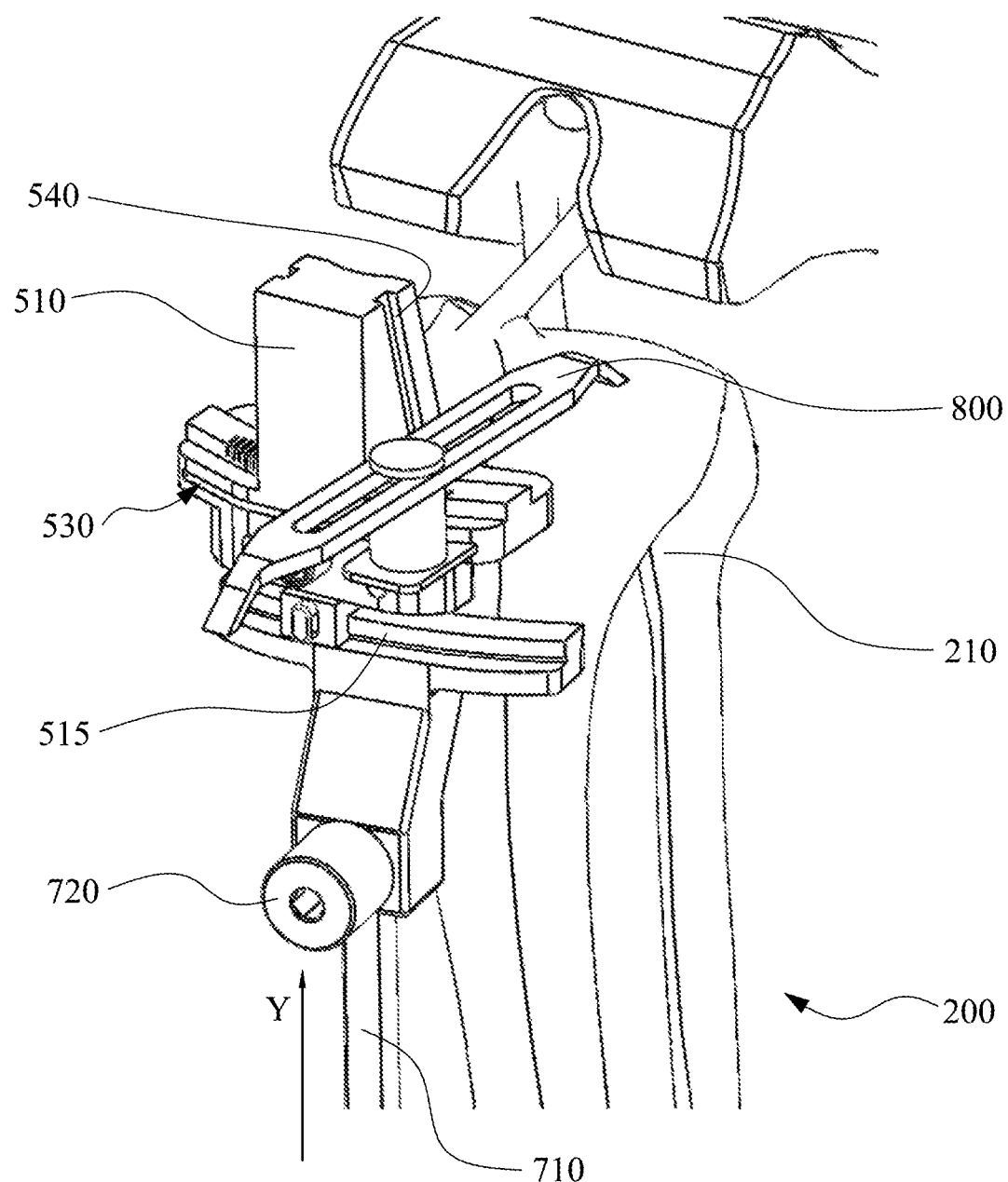
FIG. 17 is a perspective view showing the usage of a tibia resection depth stylus for measuring the height of the tibia cut guide relative to the tibia.

FIG. 17 is a perspective view showing the usage of a tibia resection depth stylus 800 for measuring the height of the tibia cut guide 510 relative to the tibia 200. Or more specifically, the tibia resection depth stylus 800 is used for measuring the height of the tibia cut guide 510 relative to the proximal tibial plateau. In other words, the depth of the resection based on the lowest point of the medial and lateral plateaus of the tibia 200 is measured. As a measuring tool, each end of the tibia resection depth stylus 800 measures a different resection depth. As shown in FIG. 17, the step (1) includes the following sub-steps:

(1.1) Mounting the EM rod 710 to the tibia 200, provided that the EM rod 710 includes a height adjustment knob 720 for fastening the intermediate component 515 to the EM rod 710. Technically speaking, the height is set by a knob (not shown in FIG. 23) which is right under the height adjustment knob 720 on the other end of the EM rod 710. The EM rod 710 lines parallel with respect to the longitudinal direction Y of the tibia.

(1.2) Attaching the intermediate component 515 to the EM rod 710.

(1.3) Connecting the tibia cut guide 510 to the intermediate component 515.

(1.4) Finding a height of the tibia cut guide 510 relative to the tibia 200. As mentioned above, the depth of the resection based on the lowest point of the medial and lateral plateaus of the tibia 200 is measured.

(1.5) Fastening the height adjustment knob 720 of the EM rod 710 to fasten the intermediate component 515 to the EM rod 710 to maintain the height found.

To be more specific, the step (1.4) includes the following sub-steps:

(1.4.1) Inserting the tibia resection depth stylus 800 into the blade slot 530 of the tibia cut guide 510.

(1.4.2) Measuring the height of the tibia cut guide 510 relative to the tibia 200.

In practical applications, the tibia resection depth stylus 800 can be used on both the medial and lateral sides of the tibia 200. By using the tibia resection depth stylus 800, a measured resection can be obtained.

Figure 18:
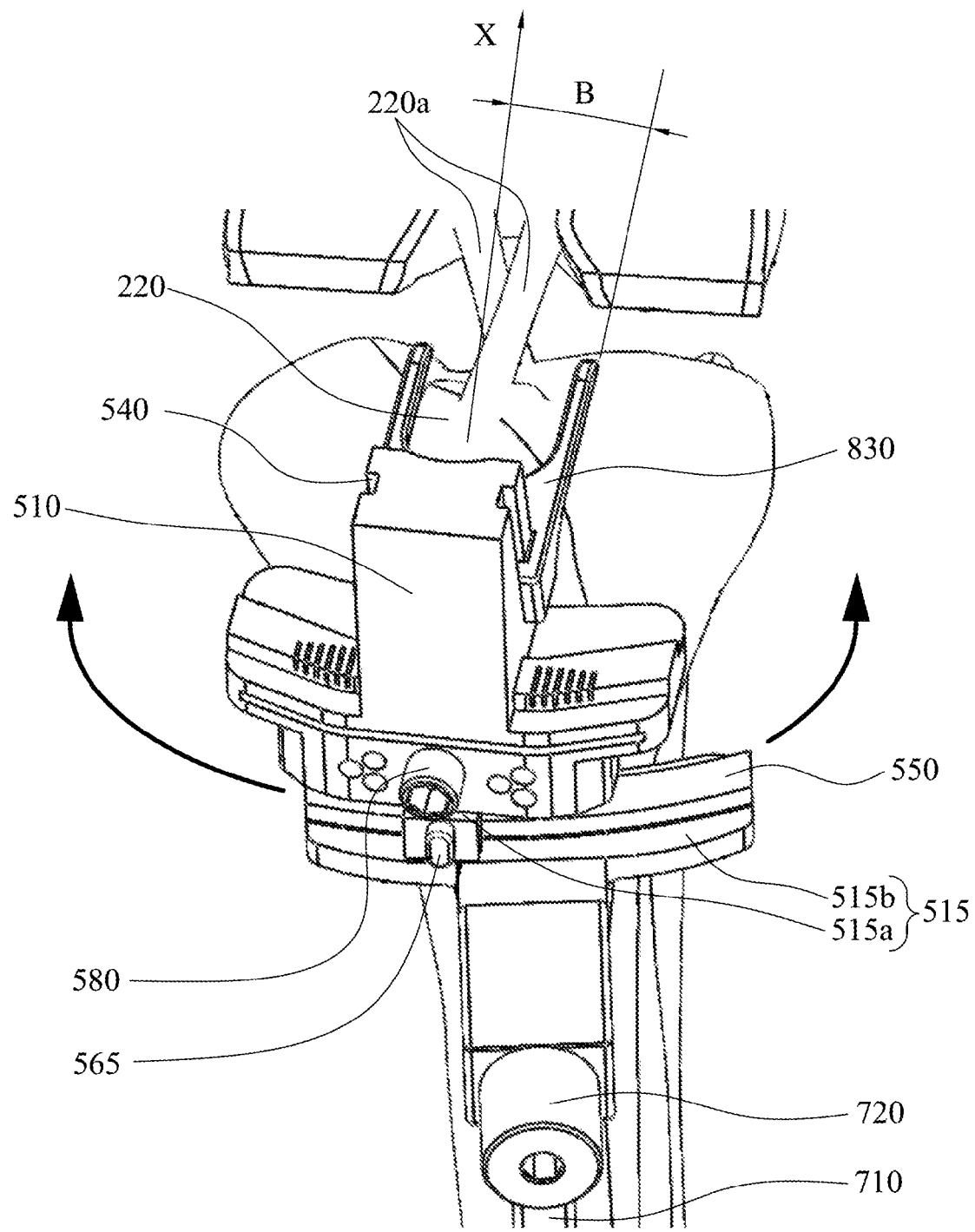
FIG. 18 is a perspective view showing a pattern of sliding of a first external rotation guide of the intermediate component relative to a second external rotation guide of the intermediate component to find a second angle of a first visual reference (VR) guide relative to the anterior-posterior direction.

FIG. 18 is a perspective view showing a pattern of sliding of a first external rotation guide 515a of the intermediate component 515 relative to a second external rotation guide 515b of the intermediate component 515 to find a second angle B of a first visual reference (VR) guide 830 relative to the anterior-posterior direction X. As shown in FIG. 18, the intermediate component 515 includes the first external rotation guide 515a and the second external rotation guide 515b. The first external rotation guide 515a is connected with the tibia cut guide 510 and the second external rotation guide 515b is attached to the EM rod 710. To be specific, the step (1) includes the following sub-steps:

(1.1) Mounting the EM rod 710 to the tibia 200.

(1.2) Attaching the second external rotation guide 515b of the intermediate component 515 to the EM rod 710.

(1.3) Connecting the tibia cut guide 510 to the first external rotation guide 515a of the intermediate component 515, provided that the first external rotation guide 515a is slidably connected with the second external rotation guide 515b.

(1.6) Finding the second angle B of the tibia cut guide 510 relative to the anterior-posterior direction X of the tibia 200 to spare the bi-cruciate ligaments 220a (i.e., the anterior cruciate ligament and the posterior cruciate ligament) and to guard the tibial eminence 220 and fixing the tibia cut guide 510 relative to the tibia 200 based on the second angle B found.

To be more specific, the step (1.6) includes the following sub-steps:

(1.6.1) Engaging slidably a first visual reference (VR) guide 830 with the first rail 540 of the tibia cut guide 510 such that the first VR guide 830 moves linearly to and away from the tibia 200 along the first rail 540.

(1.6.2) Adjusting the tibia cut guide 510 to find the second angle B of the first VR guide 830 relative to the anterior-posterior direction X to guard the tibial eminence 220.

Figure 19:
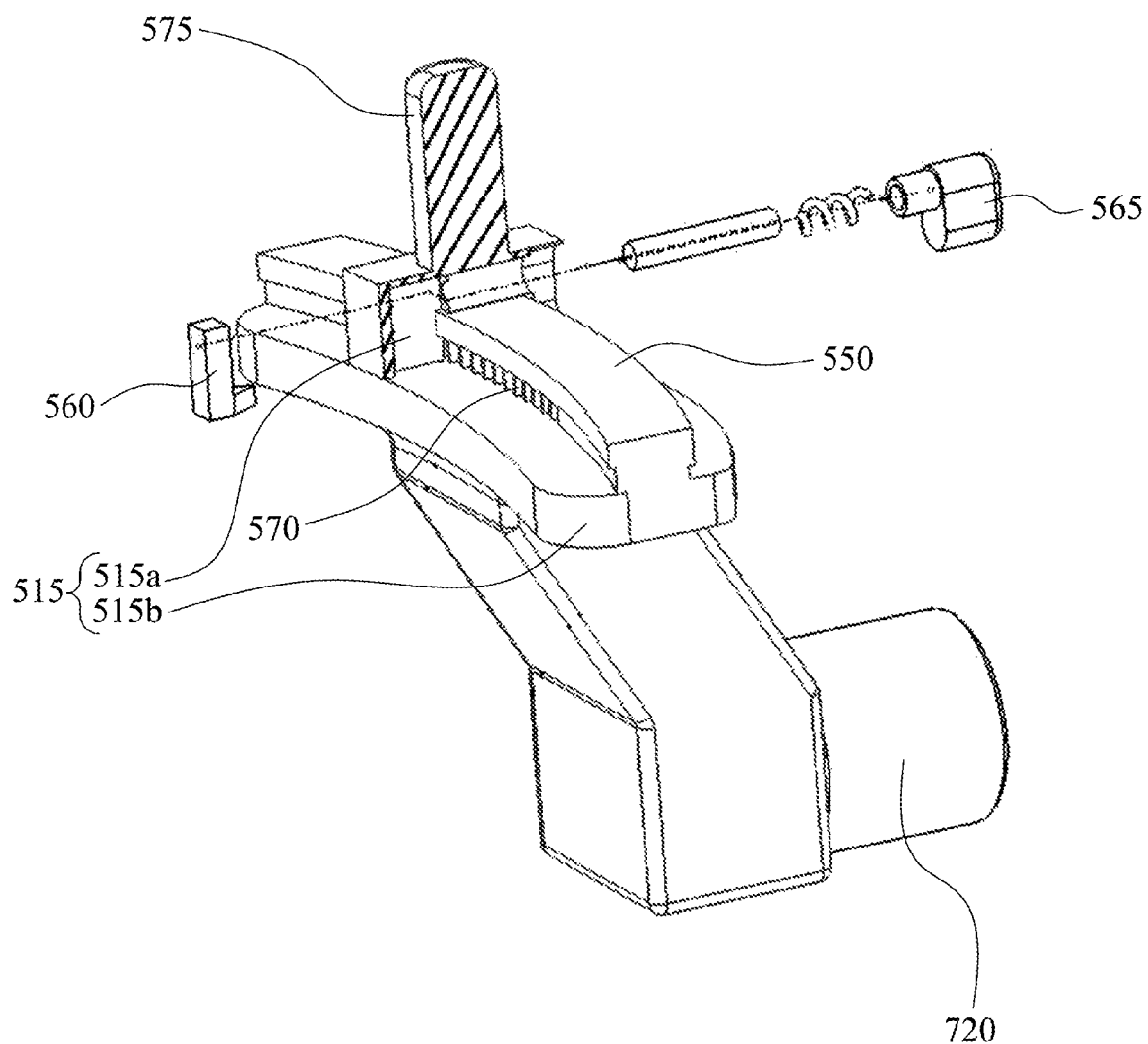
FIG. 19 is a partially-exploded view of the first external rotation guide of FIG. 18.

FIG. 19 is a partially-exploded view of the first external rotation guide 515a of FIG. 18. As shown in FIGS. 18-19, the tibia cut guide 510 (shown in FIG. 18) is connected with the first external rotation guide 515a and the first external rotation guide 515a is slidably engaged with the second external rotation guide 515b. The second external rotation guide 515b includes a second rail 550 such that the first external rotation guide 515a can slide along the second rail 550 relative to the second external rotation guide 515b. The first external rotation guide 515a includes an engaging pin 560 (shown in FIG. 19) connected with a release button 565, and the second external rotation guide 515b includes a plurality of teeth 570 (shown in FIG. 19). When an engagement is formed between the engaging pin 560 and the teeth

570, the position of the first external rotation guide 515a relative to the second external rotation guide 515b is fixed.

To be specific, when the first external rotation guide 515a slides along the second rail 550 relative to the second external rotation guide 515b, the step (1.6.2) includes the following steps:

(1.6.2.1) Pressing on the release button 565 to release the engagement between the engaging pin 560 and the teeth 570, so as to allow the first external rotation guide 515a to slide along the second rail 550 relative to the second external rotation guide 515b to find the second angle B.

(1.6.2.2) Releasing the release button 565 to make the engagement between the engaging pin 560 and the teeth 570 to fix the position of the first external rotation guide 515a relative to the second external rotation guide 515b after the second angle B is found.

Figure 20:
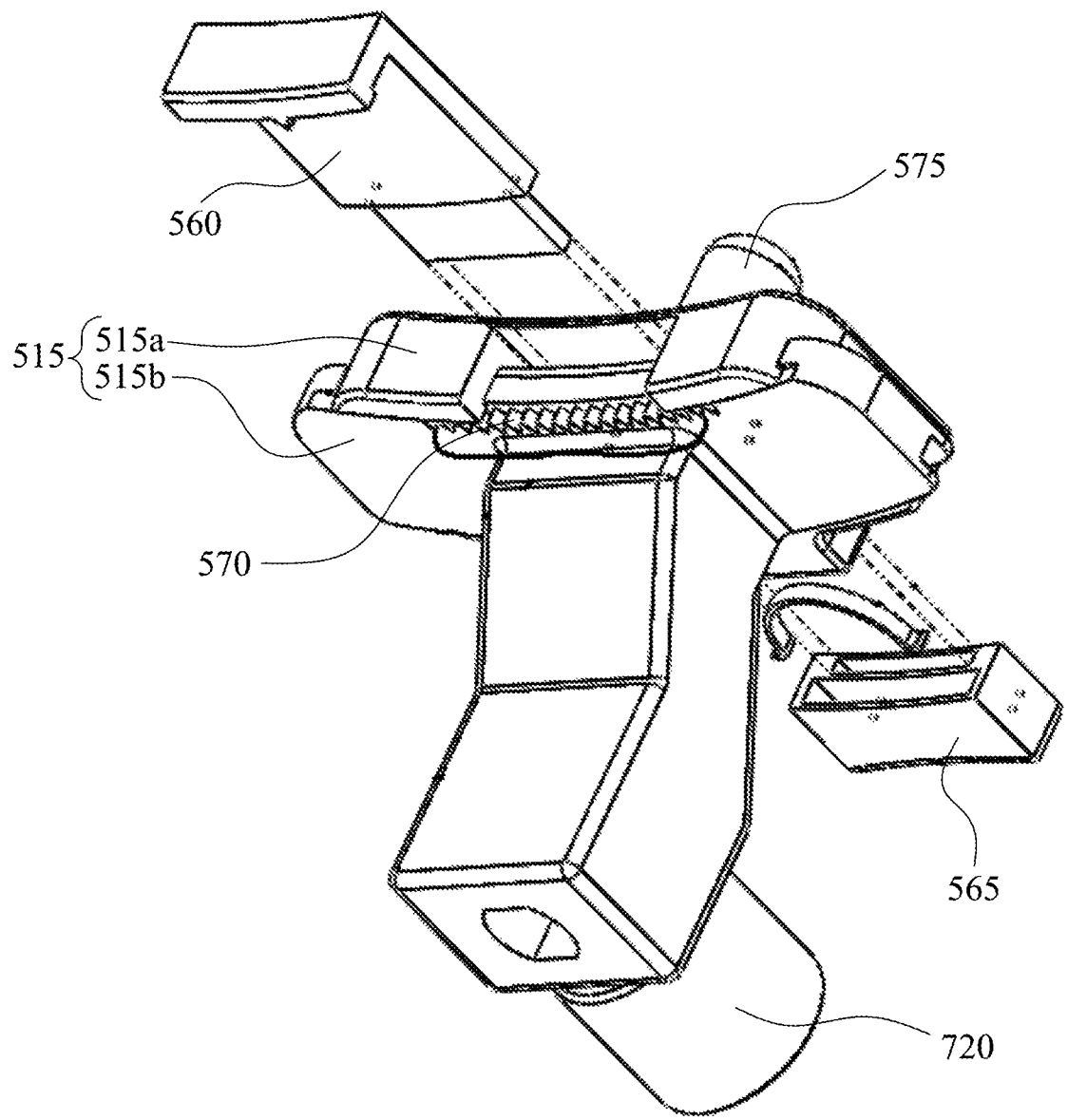
FIG. 20 is a partially-exploded view of another arrangement of the first external rotation guide of FIG. 18.

FIG. 20 is a partially-exploded view of another arrangement of the first external rotation guide 515a of FIG. 18. As shown in FIG. 20, with the major function remains the same, the physical structures of the engaging pin 560 and the release button 565 are different from those in FIG. 19. However, these physical structures of the engaging pin 560 and the release button 565 do not intend to limit the present disclosure.

Figure 21:
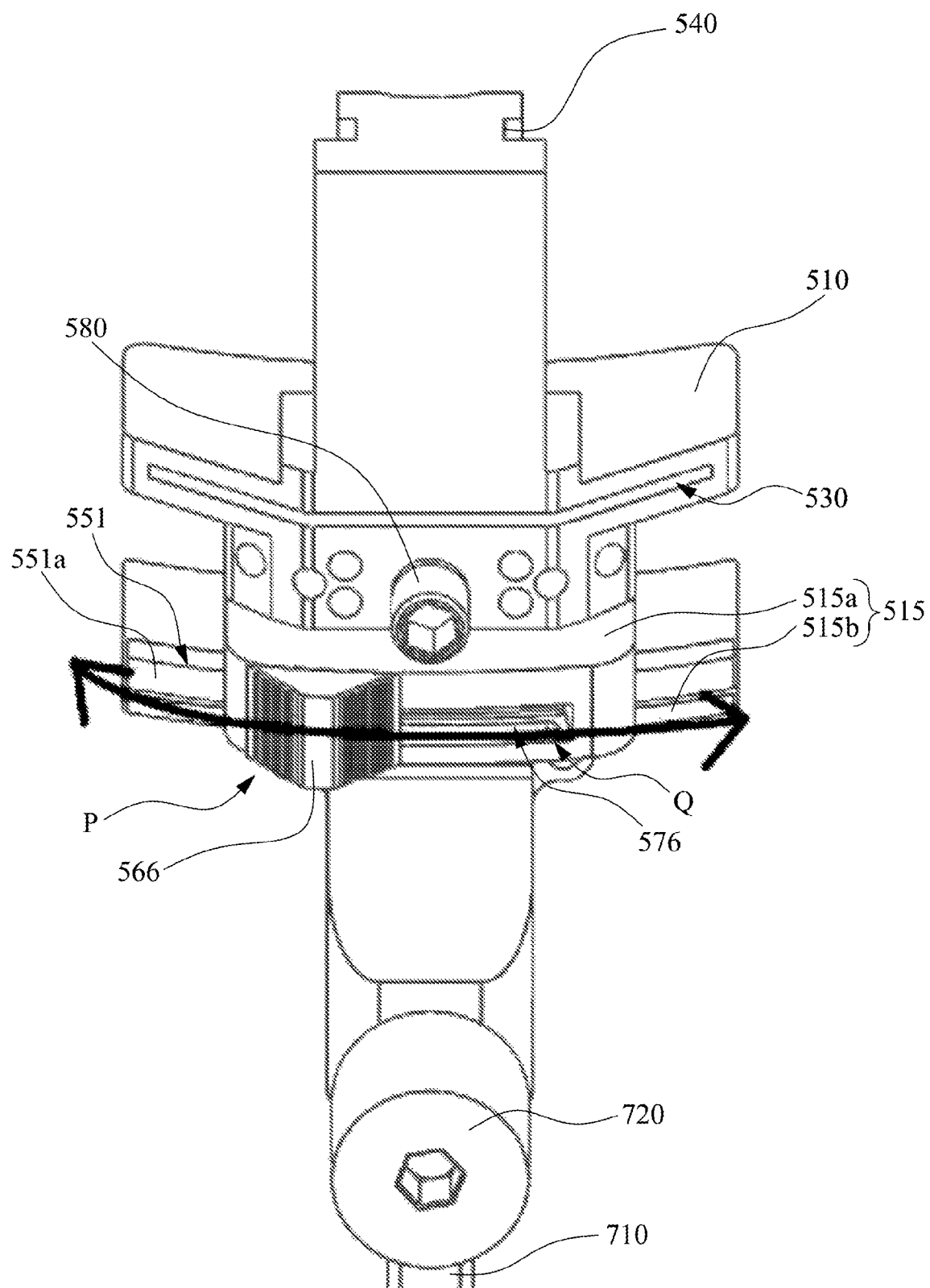
FIG. 21 is a front view showing a braking mechanism of the first external rotation guide.
Figure 22:
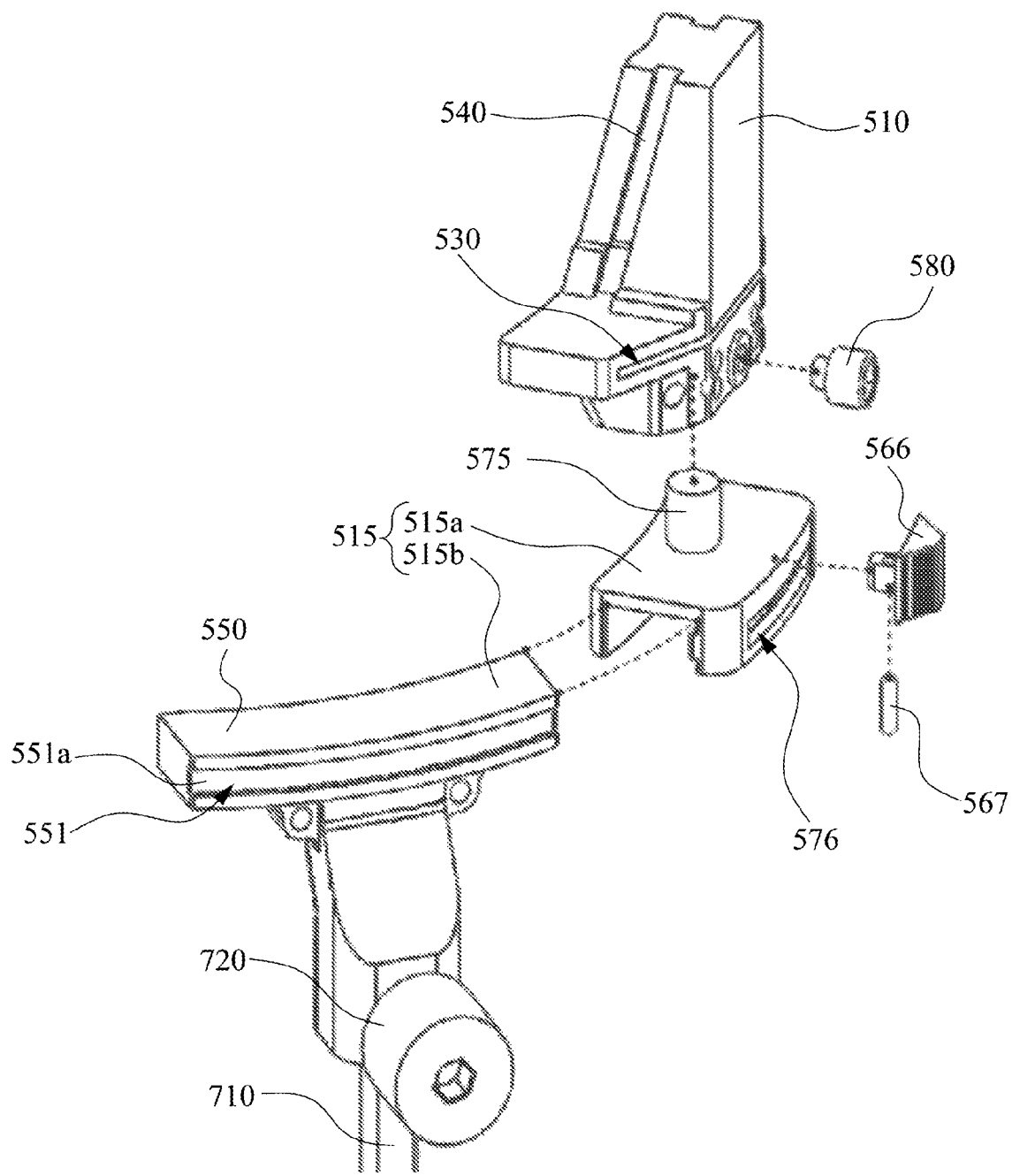
FIG. 22 is a perspective view showing the relation of connection between the tibia cut guide, the first external rotation guide and the second external rotation guide of FIG. 21.

FIG. 21 is a front view showing a braking mechanism of the first external rotation guide 515a. FIG. 22 is a perspective view showing the relation of connection between the tibia cut guide 510, the first external rotation guide 515a and the second external rotation guide 515b of FIG. 21. As shown in FIGS. 21-22, the second external rotation guide 515b has a channel 551 at a side along a sliding direction. The first external rotation guide 515a includes a sliding button 566 and a locking pin 567. The sliding button 566 passes through a sliding slot 576 of the first external rotation guide 515a. The locking pin 567 secures the sliding button 566 to the first external rotation guide 515a and mates with a slot (not shown in the Figs.) of the first external rotation guide 515a. The slot curves towards the channel 551 at one end and away from the channel 551 at the other end, such that the sliding button 566 presses on a compression surface 551a of the channel 551 and the relative position of the first external rotation guide 515a and the second external rotation guide 515b is fixed by friction when the sliding button 566 is at a first position P of the sliding slot 576. The sliding button 566 leaves the compression surface 551a when the sliding button 566 is at a second position Q of the sliding slot 576 opposite to the first position P. In practical applications, the release button can also be in the form of a screw, a clamp, a lever or a hinge tab. However, this does not intend to limit the present disclosure.

To be specific, when the first external rotation guide 515a slides along the second rail 550 relative to the second external rotation guide 515b, the step (1.6.2) includes the following steps:

(1.6.2.3) Moving the sliding button 566 to the second position Q to leave the sliding button 566 from the compression surface 551a of the channel 551, so as to allow the first external rotation guide 515a to slide along the second rail 550 relative to the second external rotation guide 515b to find the second angle B.

(1.6.2.4) Moving the sliding button 566 to the first position P to press the sliding button 566 on the compression surface 551a of the channel 551 to fix the position of the first external rotation guide 515a relative to the second external rotation guide 515b after the second angle B is found.

Figure 23:
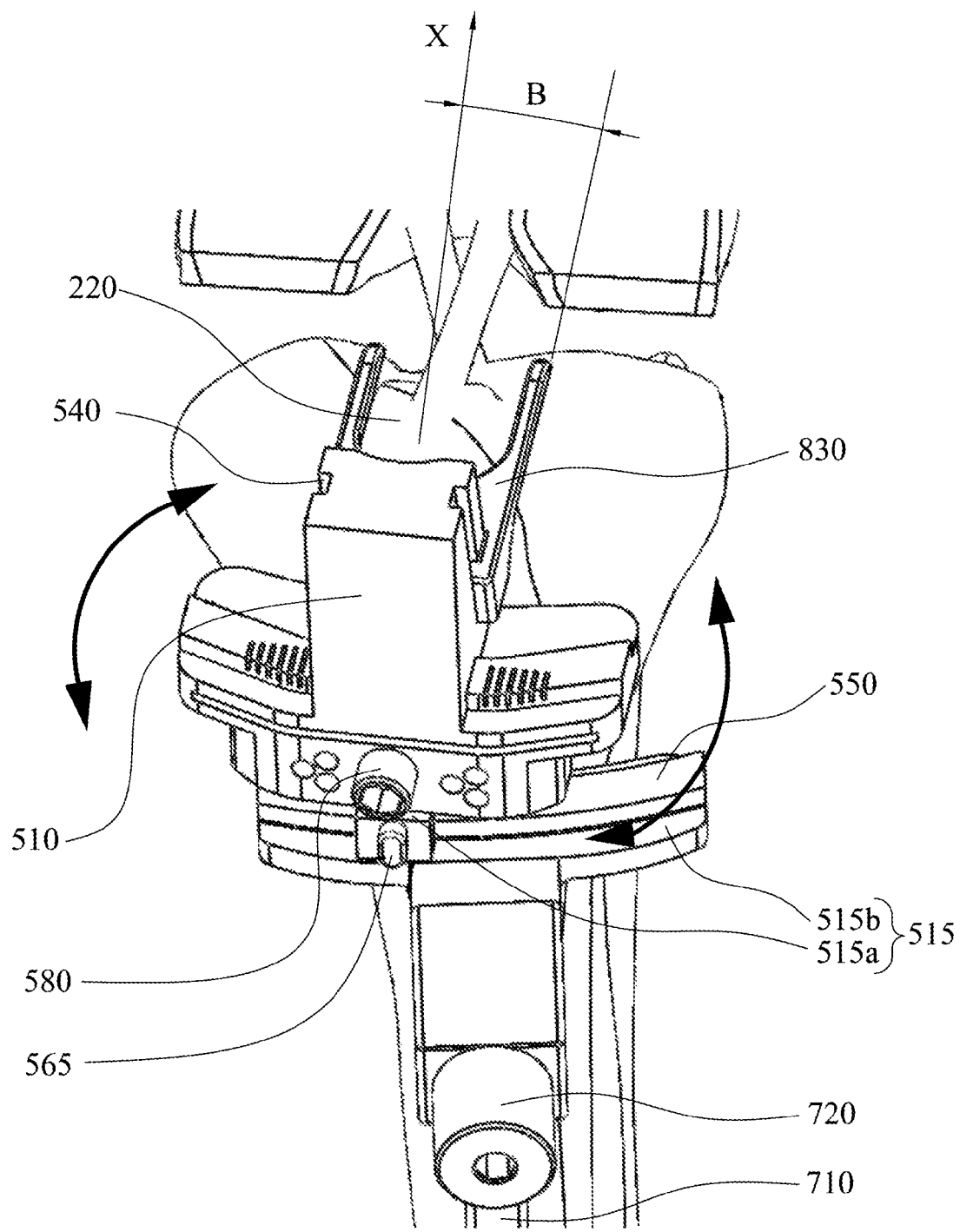
FIG. 23 is a perspective view showing a pattern of rotation of the tibia cut guide relative to the first external rotation guide of the intermediate component to find the second angle of a first visual reference (VR) guide relative to the anterior-posterior direction.

FIG. 23 is a perspective view showing a pattern of rotation of the tibia cut guide 510 relative to the first external rotation guide 515a of the intermediate component 515 to find the second angle B of a first visual reference (VR) guide 830 relative to the anterior-posterior direction X. As shown in FIGS. 19-20 and 22, on the other hand, the first external rotation guide 515a includes a rotary structure 575 such that the tibia cut guide 510 can rotate about itself relative to the first external rotation guide 515a. Moreover, as shown in FIGS. 18 and 21-23, the tibia cut guide 510 further includes a hex nut 580.

To be specific, when the tibia cut guide 510 rotates about itself, the step (1.6.2) includes the following steps:

(1.6.2.5) Rotating the tibia cut guide 510 about itself relative to the first external rotation guide 515a.

(1.6.2.6) Fastening the hex nut 580 to fix the tibia cut guide 510 relative to the first external rotation guide 515a after the second angle B is found.

Figure 24:
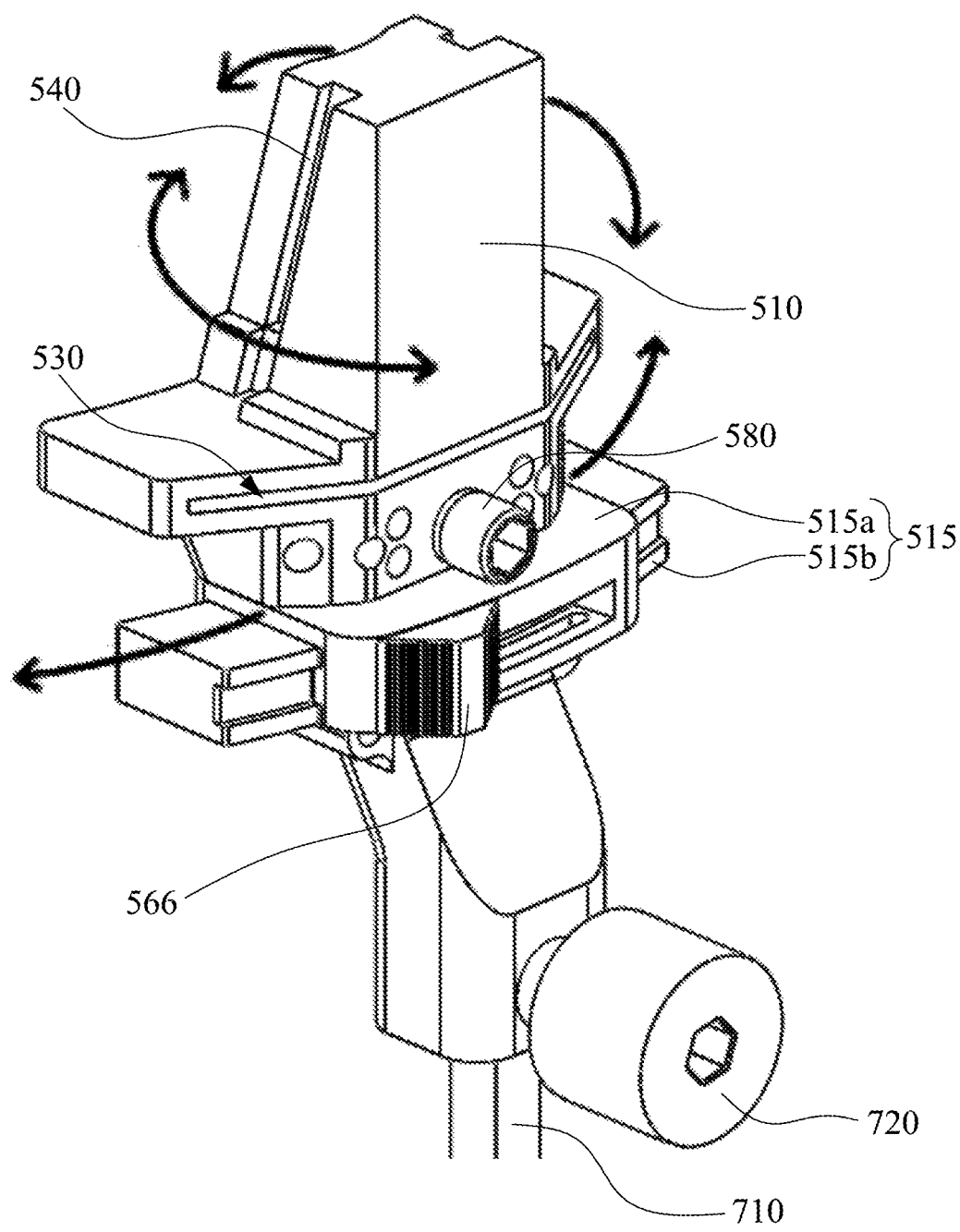
FIG. 24 is a perspective view showing both the pattern of sliding of the first external rotation guide relative to the second external rotation guide and the pattern of rotation of the tibia cut guide relative to the first external rotation guide.

FIG. 24 is a perspective view showing both the pattern of sliding of the first external rotation guide 515a relative to the second external rotation guide 515b and the pattern of rotation of the tibia cut guide 510 relative to the first external rotation guide 515a. In practical applications, as shown in FIG. 24, the action of sliding of the first external rotation guide 515a relative to the second external rotation guide 515b and the action of rotation of the tibia cut guide 510 relative to the first external rotation guide 510a are independent of each other. As a result, both actions can occur separately or simultaneously in order to find the second angle B of a first visual reference (VR) guide 830 relative to the anterior-posterior direction X.

Figure 25:
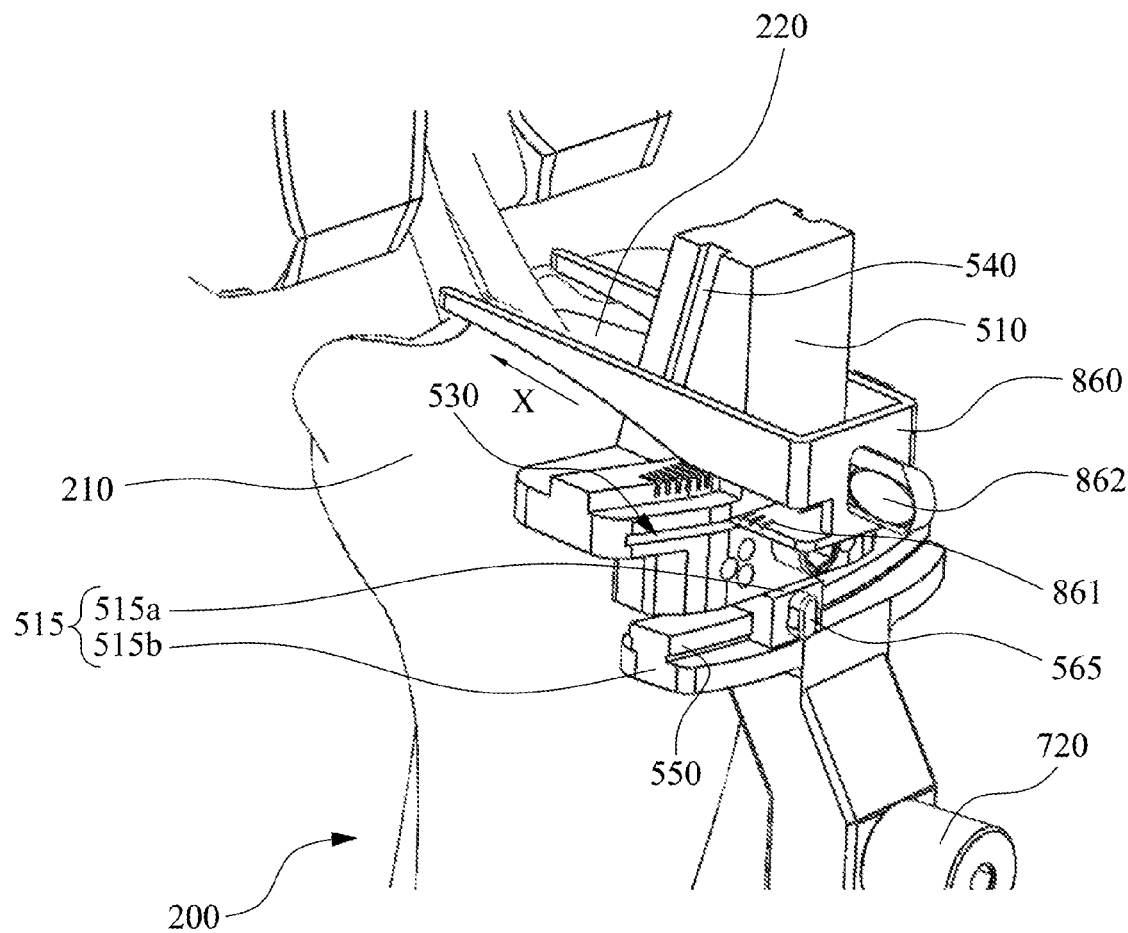
FIG. 25 is a perspective view showing the movement of the second visual reference (VR) guide along the anterior-posterior direction to find the anterior-posterior (AP) length for the tibial stem punch and guard.
Figure 26:
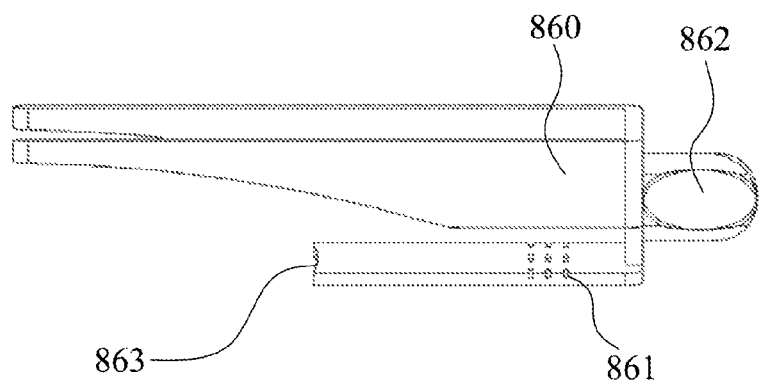
FIG. 26 is a perspective view of the second VR guide of FIG. 25.

FIG. 25 is a perspective view showing the movement of the second visual reference (VR) guide 860 along the anterior-posterior direction X to find the anterior-posterior (AP) length for the tibial stem punch and guard 520. FIG. 26 is a perspective view of the second VR guide 860 of FIG. 25. Theoretically, the tibia cut guide 510 is meant to be flush against the anterior portion 250 of the tibia 200. However, with unpredictable anatomy and conditions, the second VR guide 860 is used to get an approximate measurement of how far the tibia cut guide 510 is from being flush with the anterior portion 250. As shown in FIGS. 25-26, the second VR guide 860 has a plurality of markers 861 lining up with the entrance of the blade slot 530 of the tibia cut guide 510. In practice, the markers 861 can be color coded or numbered along with the tibial stem punch and guard 520 (not shown in FIGS. 25-26) to indicate the proper length of the tibial stem punch and guard 520 to help surgeons identify clearly which tibial stem punch and guard 520 should be used. A grip tab 862 of the second VR guide 860 is used to help the user operate the second VR guide 860. To be specific, the step (1) includes the following sub-steps:

(1.1) Mounting the EM rod 710 to the tibia 200.

(1.2) Attaching the second external rotation guide 515b of the intermediate component 515 to the EM rod 710.

(1.3) Connecting the tibia cut guide 510 to the first external rotation guide 515a of the intermediate component 515, provided that the first external rotation guide 515a is slidably connected with the second external rotation guide 515b.

(1.7) Moving the second VR guide 860 with the markers 861 along the anterior-posterior direction X of the tibia 200 through the blade slot 530 of the tibia cut guide 510 until a referencing edge 863 of the second VR guide 860 touches the anterior portion 250 of the tibia 200, so as to find an AP length for the tibial stem punch and guard 520. Once the referencing edge 863 touches the anterior portion 250 of the tibia 200, the surgeon should visually determine which of the markers 861 is at the very front of the tibia cut guide 510.

The marker 861 determined correlates directly with the AP length of the tibial stem punch and guard 520.

Figure 27:
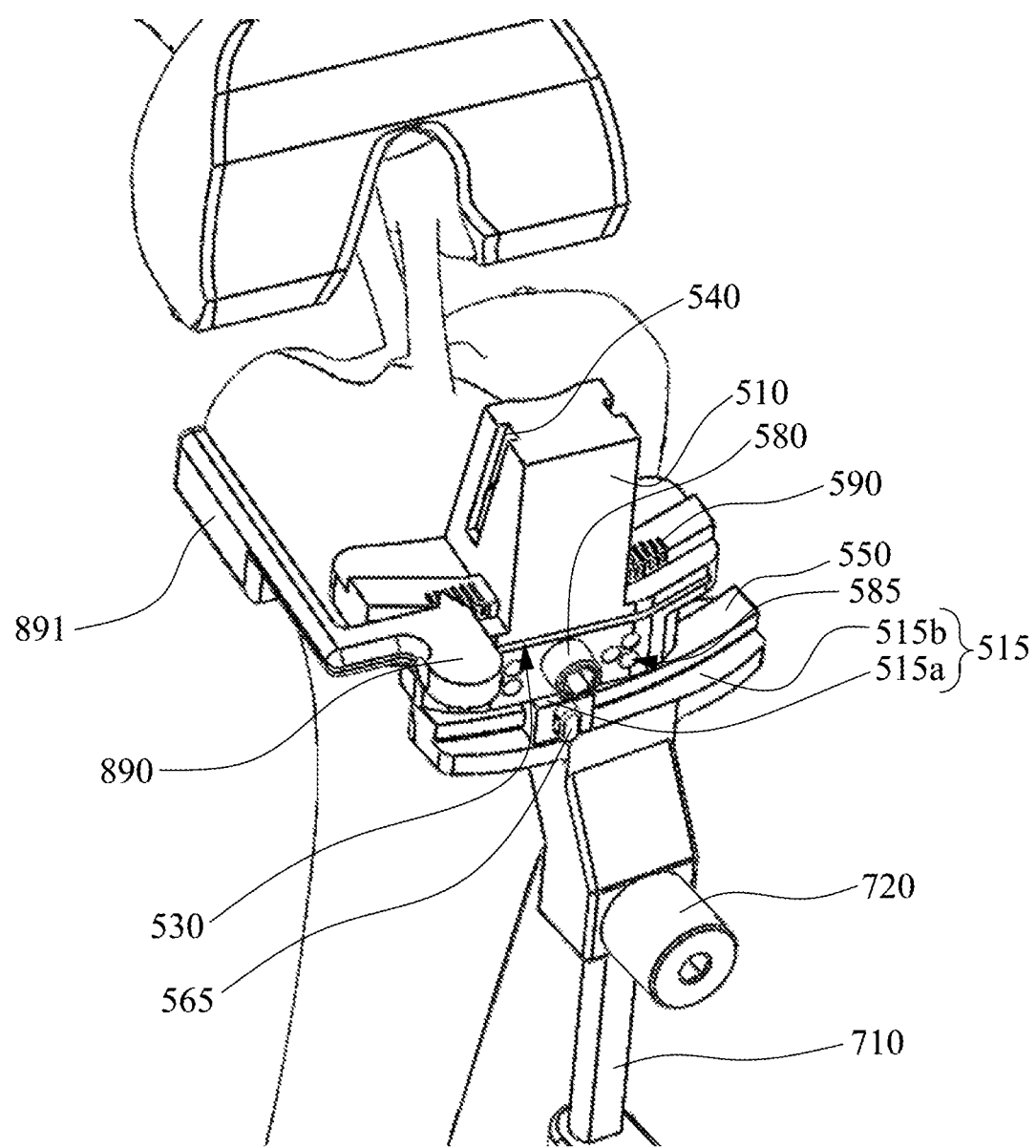
FIG. 27 is a perspective view showing the usage of a medial lateral (ML) sizing stylus for measuring a ML width of the tibia.
Figure 28:
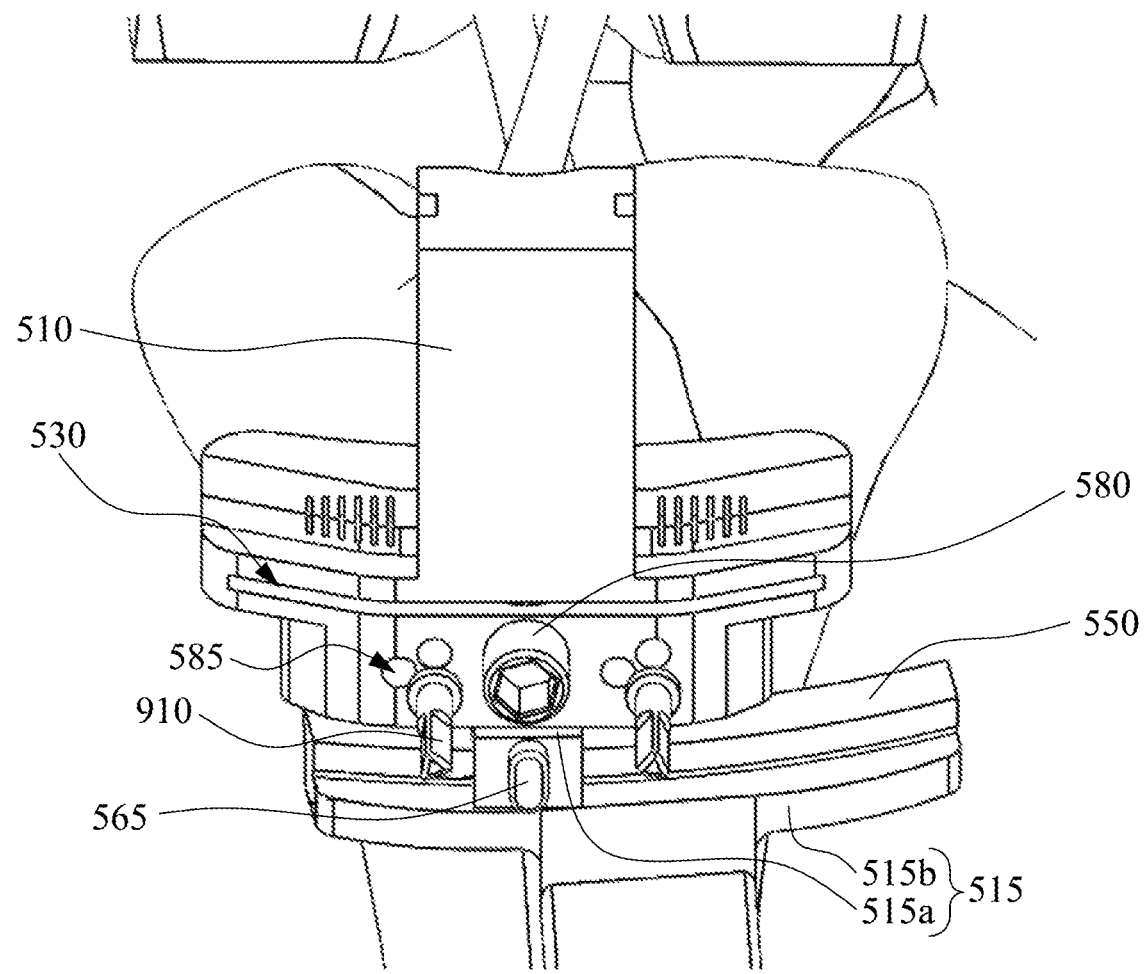
FIG. 28 is a perspective view showing the usage of speed pins to fix the position of the tibia cut guide relative to the first external rotation guide.

FIG. 27 is a perspective view showing the usage of a medial lateral (ML) sizing stylus 890 for measuring a ML width of the tibia 200. FIG. 28 is a perspective view showing the usage of speed pins 910 to fix the position of the tibia cut guide 510 relative to the first external rotation guide 515a. The ML sizing stylus 890 has a spring-loaded arm 891 that is armed with a rack and pinion gear set up (not shown in FIGS. 27-28) that will assist in centering the tibia cut guide 510. As shown in FIGS. 27-28, the tibia cut guide 510 has at least a speed pin hole 585 communicated with a locking hole (not shown in FIGS. 27-28) inside the first external rotation guide 515a.

To be specific, the step (1) includes the following sub-steps:

(1.1) Mounting the EM rod 710 to the tibia 200.

(1.2) Attaching the second external rotation guide 515b of the intermediate component 515 to the EM rod 710.

(1.3) Connecting the tibia cut guide 510 to the first external rotation guide 515a of the intermediate component 515, provided that the first external rotation guide 515a is slidably connected with the second external rotation guide 515b.

(1.8) Measuring the ML width of the tibia 200 by the ML sizing stylus 890 engaged with the blade slot 530 of the tibia cut guide 510. The front portion of the ML sizing stylus 890 is a touch probe that sits tangent against the side of the tibia 200. Once the probe is in contact with the side of the tibia, the portion of the probe that is engaged with the tibia cut guide 520 has an indicator that points to the markers 590 of the tibia cut guide 520. The marker 590 pointed is in correspondence with the size of the tibial base plate 100 (not shown in FIGS. 27-28) that will later be attached on the resected surface S1 of the tibia 200.

(1.9) Inserting the speed pin 910 into the speed pin hole 585 of the tibia cut guide 510 and the locking hole inside the first external rotation guide 515a to fix the position of the tibia cut guide 510 relative to the first external rotation guide 515a after the ML width is found. The quantity of the speed pin 910 to be used can be more than one. However, this does not intend to limit the present disclosure.

Figure 29:
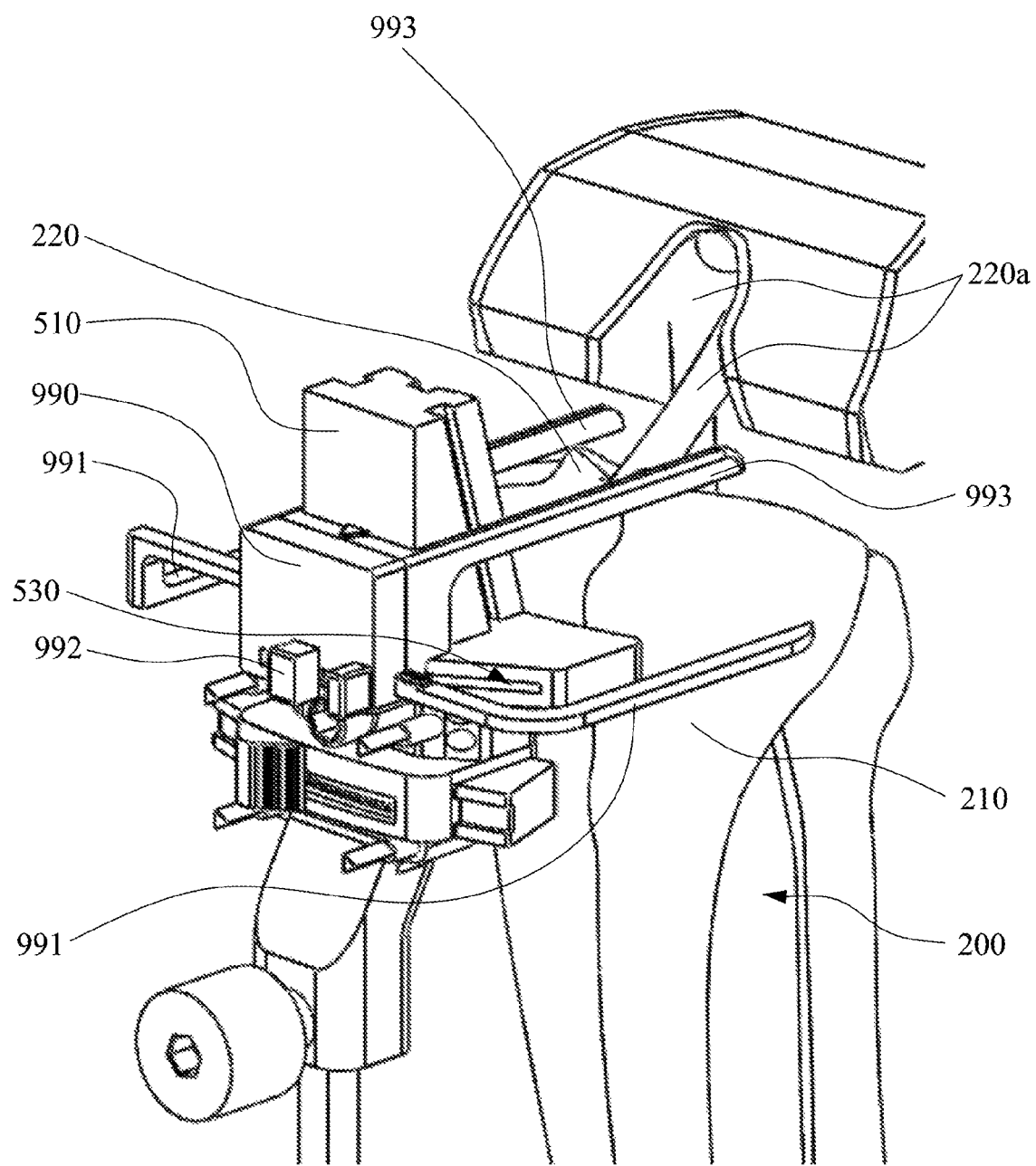
FIG. 29 is a perspective view showing the usage of a medial lateral (ML) centering device for centering the tibia cut guide relative to the ML width and the location of the tibial eminence.

FIG. 29 is a perspective view showing the usage of a medial lateral (ML) centering device 990 for centering the tibia cut guide 510 relative to the ML width and the location of the tibial eminence 220. As shown in FIG. 29, the ML centering device 990 includes a pair of arms 991 and a button 992. In practical applications, the arms 991 are located adjacent to the tibia 200 and the bottom surface of each of the arms 991 is at the same plane/level as the bottom surface of the blade slot 530 of the tibia cut guide 510. During operation, when the button 992 is pushed, the arms 991 are opened so that the arms 991 can be adjacent to the sides of the tibia 200. In addition, the ML centering device 990 further includes a pair of forks 993, which provides another method of centering the ML centering device 990 by visual reference through the pair of forks 993. In general, the pair of forks 993 is located above the proximal end 210 of the tibia 200, allowing the surgeon to alight the ML centering device 990 such that the bi-cruciate ligaments 220a are centered within the pair of forks 993.

Figure 30:
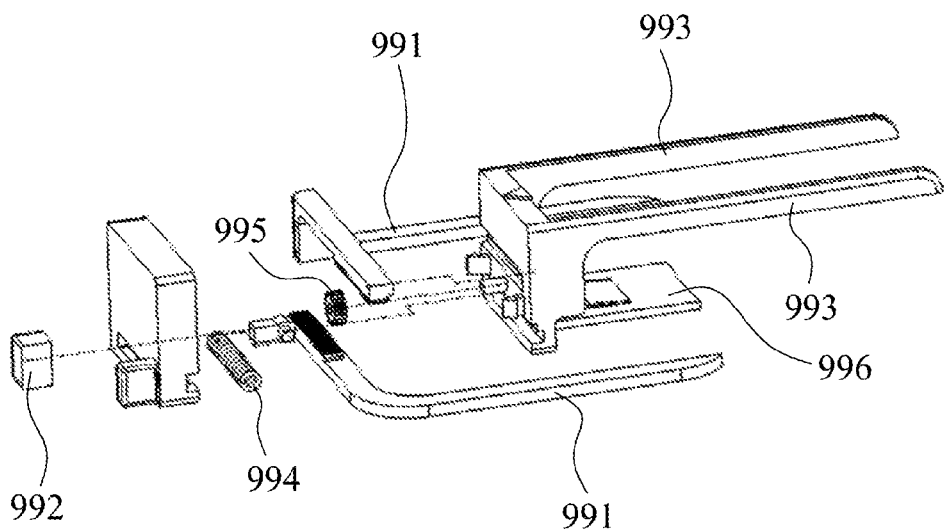
FIG. 30 is an exploded view of the ML centering device of FIG. 29.
Figure 31:
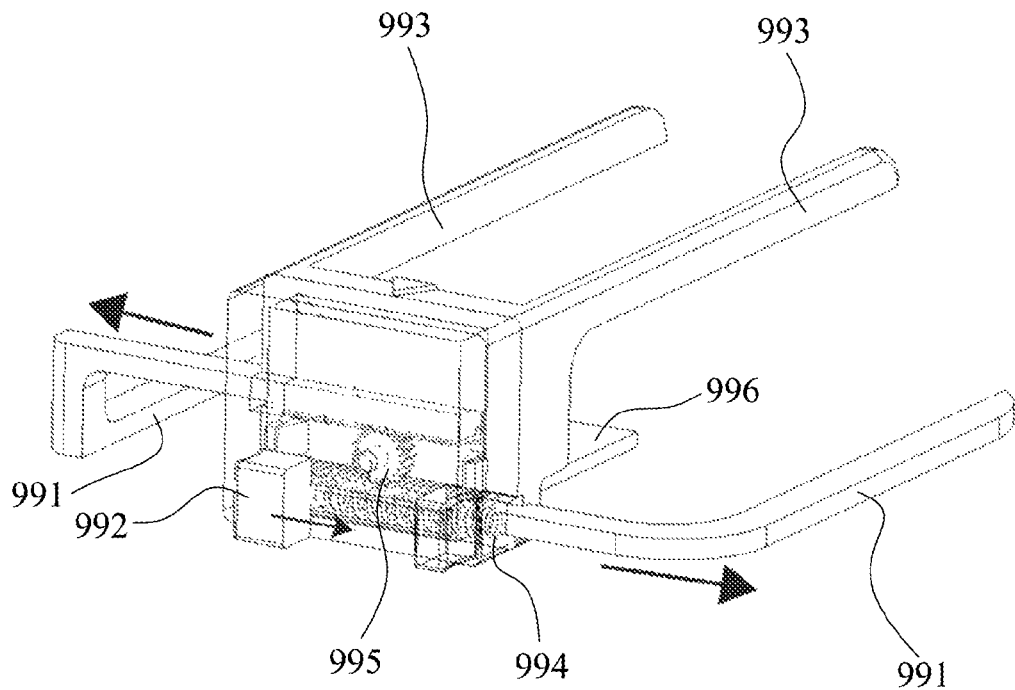
FIG. 31 is a perspective view showing the operation of the ML centering device of FIG. 29.

FIG. 30 is an exploded view of the ML centering device 990 of FIG. 29. FIG. 31 is a perspective view showing the operation of the ML centering device 990 of FIG. 29. As shown in FIGS. 30-31, the ML centering device 990 includes a spring 994 and a central gear 995. The spring 994 is attached to one of the arms 991, and the central gear 995 drives the pair of arms 991. Since the pair of arms 991 are connected to and driven by the central gear 995 through a mechanism of rack and pinion, when the ML centering device 990 is not in use, the spring 994 keeps the pair of arms 991 in a closed state. In this embodiment, since the button 992 is directly connected to one of the arms 991, when the button 992 is pushed, the arm 991 connected with the button 992 will be opened, which in turn drives the other arm 991 to open through the action of the central gear 995. When the button 992 is released, the pair of the arms 991 will return to their closed positions through the compressive force of the spring 994 acting on the pair of the arms 991. In this way, the tibia cut guide 520 can be centered relative to the medial lateral (ML) width and the location of the tibial eminence 220 by an adjustment through the push and release of the button 992 of the ML centering device 990 such that the bi-cruciate ligaments 220a are centered within the pair of forks 993 of the ML centering device 990.

In addition, the ML centering device 990 further includes a tab 996 extending in the same direction as the pair of forks 993. The tab 996 is used to insert into the blade slot 530 of the tibia cut guide 510. In this way, the tab 996 can feature as a friction fit tab which ensures a secure engagement of the ML centering device 990 with the tibia cut guide 510.

To be specific, the step (1) includes the following sub-steps:

(1.1) Mounting the EM rod 710 to the tibia 200.

(1.2) Attaching the second external rotation guide 515b of the intermediate component 515 to the EM rod 710.

(1.3) Connecting the tibia cut guide 510 to the first external rotation guide 515a of the intermediate component 515, provided that the first external rotation guide 515a is slidably connected with the second external rotation guide 515b.

(1.10) Centering the tibia cut guide 510 relative to the medial lateral (ML) width and the location of the tibial eminence 220 by an adjustment through the push and release of the button 992 of the ML centering device 990 such that the bi-cruciate ligaments 220a are centered within the pair of forks 993 of the ML centering device 990.

On the other hand, provided that at least one punch is engaged to the tibia cut guide 510 and the tibia 200, the method for attaching the tibial base plate 100 on the tibia 200 includes the following steps (it is appreciated that the sequence of the steps and the sub-steps as mentioned below, unless otherwise specified, can all be adjusted upon the actual needs, or even executed at the same time or partially at the same time):

(1) Fixing the tibia cut guide 510 to the anterior portion 250 of the tibia 200.

(7) Engaging slidably the punch with the first rail 540 of the tibia cut guide 510 such that the punch moves linearly to and away from the tibia 200 along the first rail 540. To be specific, the punch can be an external punch 521 or an internal punch 522. As mentioned above, the first rail 540 is inclined at the first angle A relative to a longitudinal direction Y along the tibia 200.

(8) Resecting a medial and lateral plateau.

(9) Impacting the punch, i.e., the external punch 521 or the internal punch 522 into the tibia 200 at the first angle A to act as a barrier guarding the tibial eminence 220 of the tibia 200 and to form the cutting slot C (shown in FIG. 2) at the tibia 200. That means, before the resected surface S1 is made in the next step, the tibial eminence 220 is already well guarded and protected.

(4) Making the resected surface S1 on the tibia 200 by the blade 610 passing through the blade slot 530 of the tibia cut guide 510 at a region outside the tibial eminence 220 as guarded by the punch, i.e., the external punch 521 or the internal punch 522. In this way, the tibial eminence 220 is well protected and will not be damaged when the resected surface S1 is made.

(5) Fixing the tibial base plate 100 on the resected surface S1 by engaging the stem 130 of the tibial base plate 100 with the cutting slot C (shown in FIG. 2) and the tibial eminence 220 of the tibia 200 being accommodated in a notch N of the tibial base plate 100. Please refer to FIG. 1 for the tibial base plate 100 being attached to the resected surface S1 at the proximal end 210 of the tibia 200.

Figure 32:
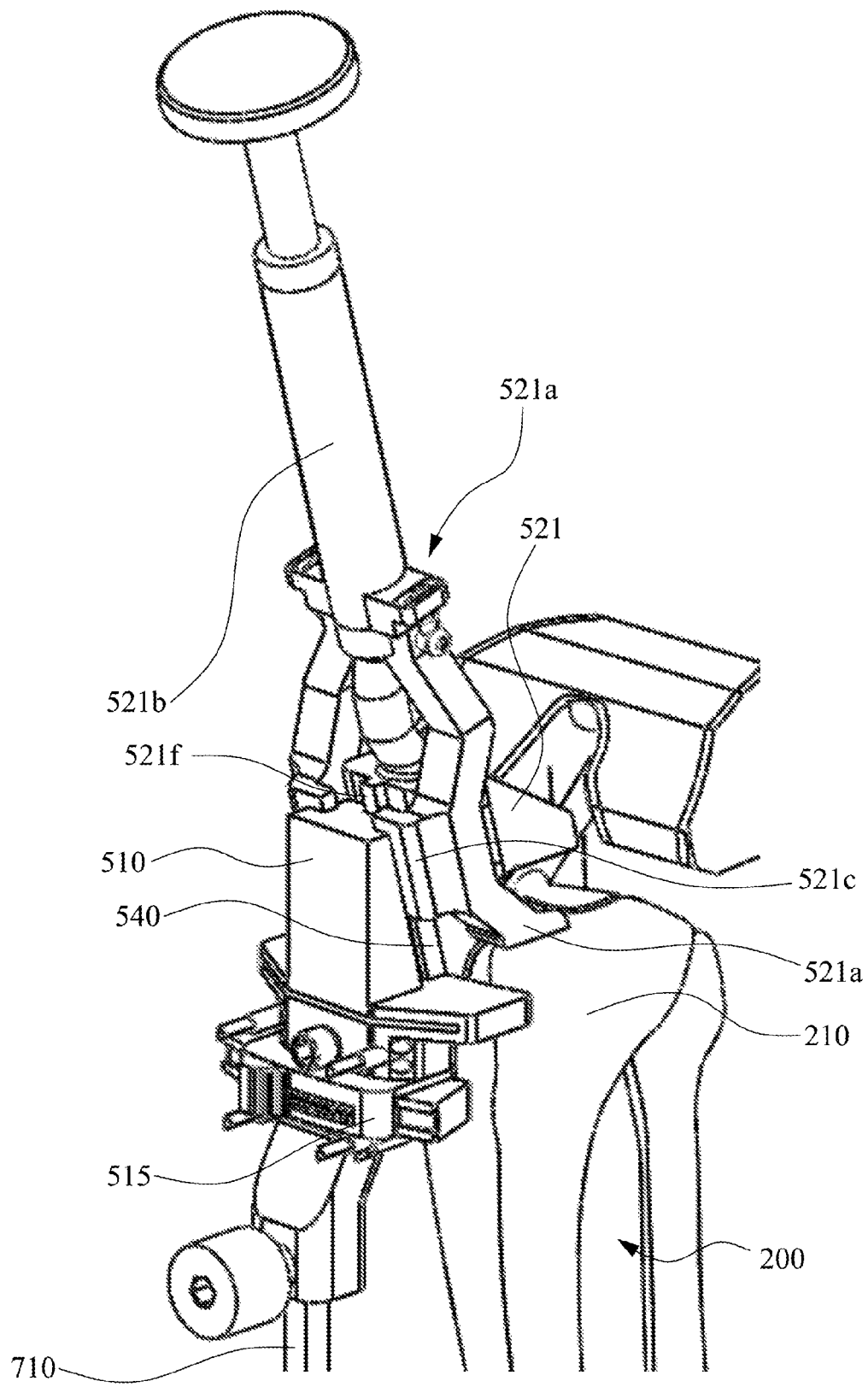
FIG. 32 is a perspective view showing the engagement of an external punch to the tibia cut guide and the proximal end of the tibia.

FIG. 32 is a perspective view showing the engagement of an external punch 521 to the tibia cut guide 510 and the proximal end 210 of the tibia 200. As shown in FIG. 32, the feet 521a of the external punch 521 come into contact with the proximal end 210 of the tibia 200. It is not designed to have both feet 521a engaged to the proximal end 210 simultaneously as a result of an unpredictable anatomy at the proximal end 210. The external punch 521 itself will be driven into the proximal end 210 under the guidance of the sheath 521b. The punch depth of the external punch 521 will be referenced off of the tibia cut guide 510 via the engaging rail 521c located on the external punch 521. In addition, the punch depth is limited by the engagement of a cut guide tab (blocked and not shown in FIG. 32) of the tibia cut guide 510 and a punch tab 521f of the external punch 521.

Figure 33:
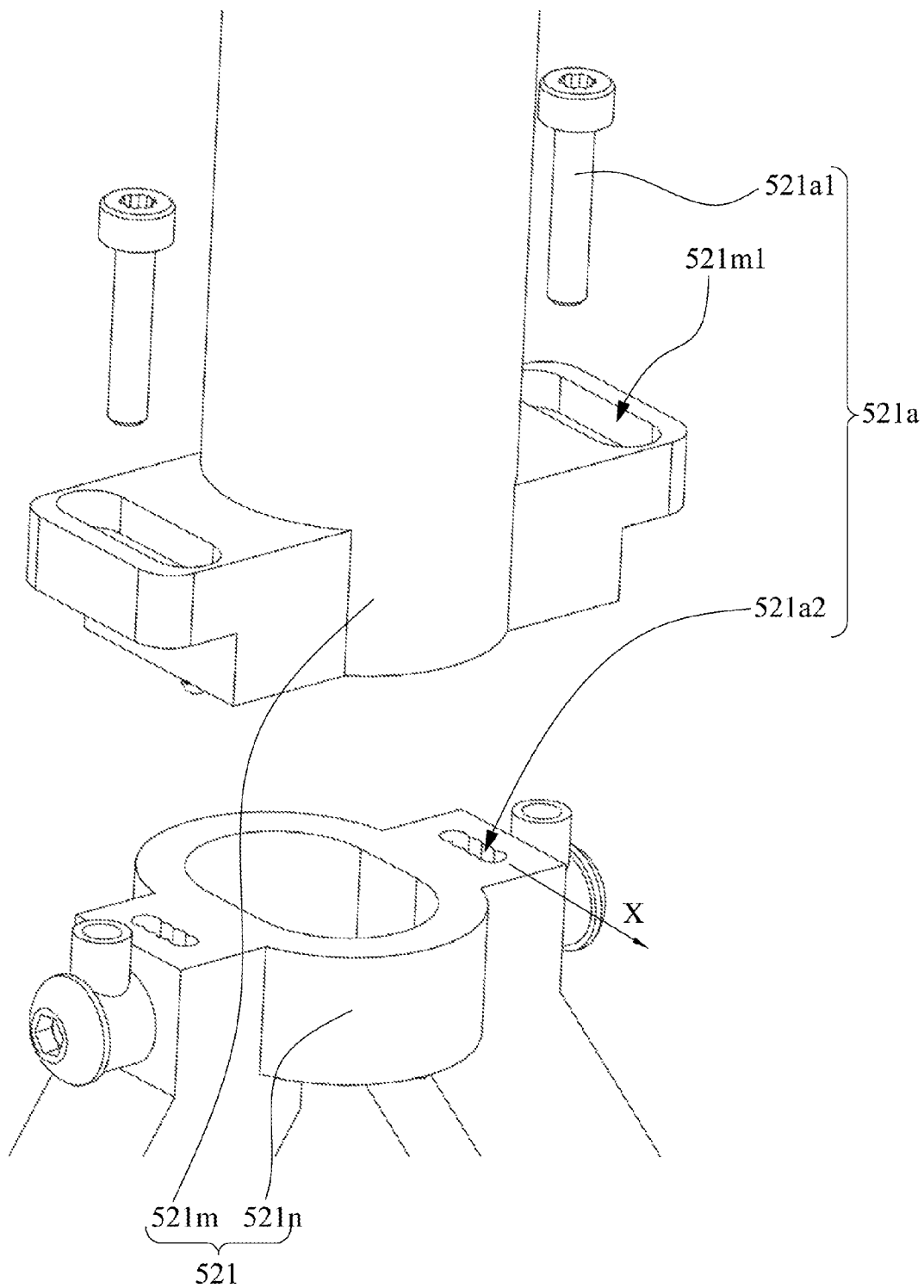
FIG. 33 is an enlarged view showing a slot-pin mechanism of the external punch.

FIG. 33 is an enlarged view showing a slot-pin mechanism 521a of the external punch 521. As shown in FIG. 33, the external punch 521 includes an upper part 521m and a lower part 521n. To be specific, the method for attaching the tibial base plate 100 on the tibia 200 further includes the following step:

(10) Calibrating the position of the upper part 521m of the external punch 521 relative to the lower part 521n of the external punch 521 in the anterior-posterior (AP) direction X.

In practical applications, prior to the engagement, the external punch 521 must be calibrated for an anterior-posterior (AP) length. As mentioned above, the external punch 521 includes the upper part 521m and the lower part 521n. The position of the upper part 521m relative to the lower part 521n in the anterior-posterior (AP) direction X can be calibrated. The external punch 521 includes the slot-pin mechanism 521a which in turn includes a pin 521a1 and a slot 521a2. The slot 521a2 is located at the lower part 521n. After the correct relative position of the upper part 521m and the lower part 521n is determined, the pin 521a1 of the slot-pin mechanism 521a is inserted through a hole 521m1 of the upper part 521m into the slot 521a2 of the slot-pin mechanism 521a, such that the relative position of the upper part 521m of the external punch 521 is fixed to the lower part 521n of the external punch 521. In this way, the AP length of the external punch 521 is calibrated. In this embodiment, the wall of the slot 521a2 is in the shape of a wave, such that the pin 521a1 can be inserted only into some particular locations in the slot 521a2. This facilitates the calibration of the external punch 521. However, this shape of the slot 521a2 does not intend to limit the present disclosure.

Figure 34:
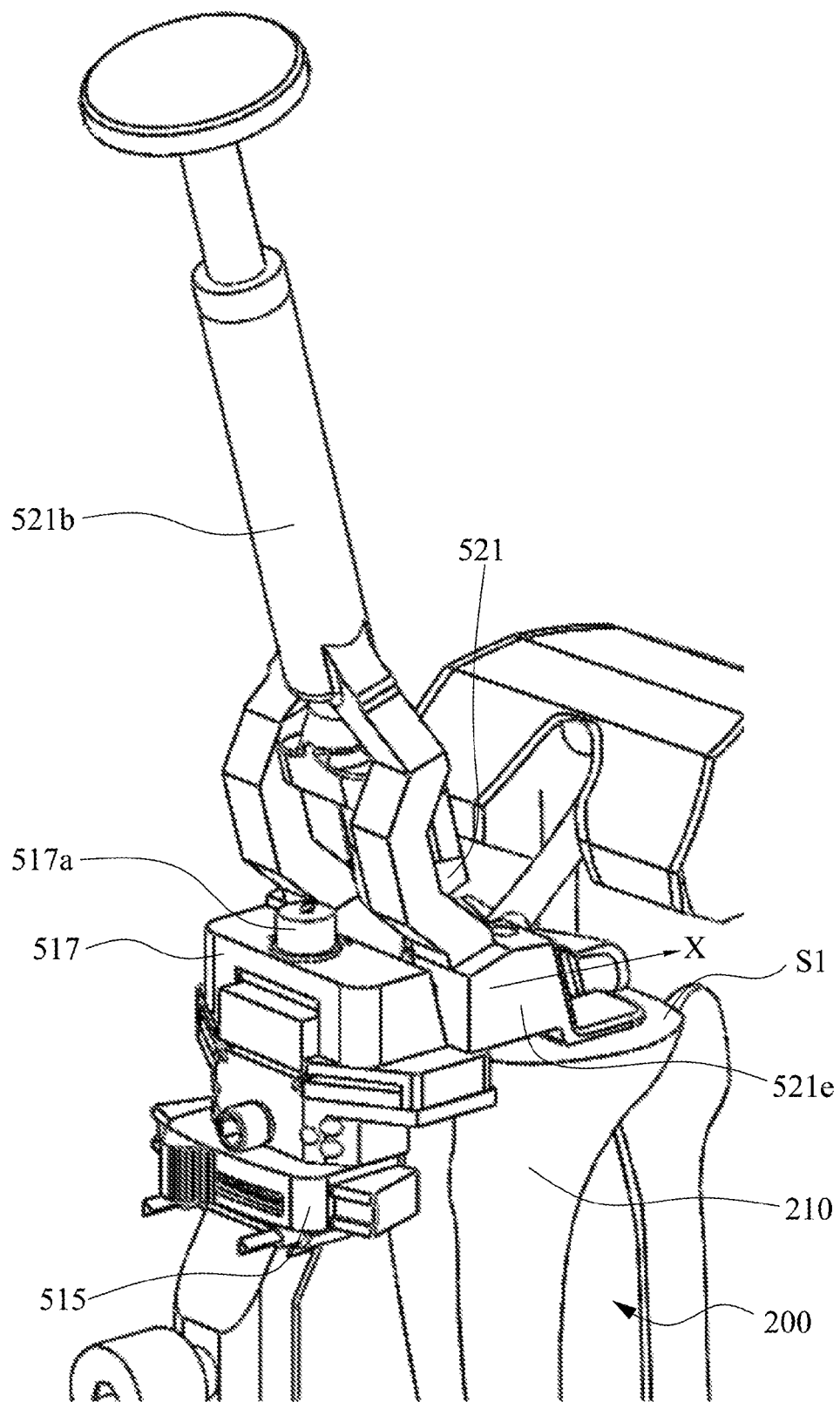
FIG. 34 is a perspective view showing the application of another external punch.

FIG. 34 is a perspective view showing the application of another external punch 521. As shown in FIG. 34, the external punch 521 features a sheath 521b with pegs (blocked and not shown in FIG. 34) to engage with the punch fixation base 521e. The surface of the punch fixation base 521e that engages with the external punch 521 is at an angle with the resected surface S1. Within the sheath 521b there is a spring (blocked and not shown in FIG. 34) to keep the external punch 521 in an armed position for impacting. The sheath 521b and the punch fixation base 521e will properly position and orient the external punch 521.

Furthermore, as shown in FIG. 34, the anterior-posterior (AP) adjustment/calibration guide 517 is slidably connected to the intermediate component 515 along the anterior-posterior direction X. In addition, the punch fixation base 521e of the external punch 521 is connected with the AP adjustment/calibration guide 517. In this way, the calibration of the external punch 521 along the anterior-posterior direction X can be carried out. When the correct position of the external punch 521 is determined, the turning knob 517a of the AP adjustment/calibration guide 517 can be rotated to fix the position of the AP adjustment/calibration guide 517 relative to the intermediate component 515.

Figure 35:
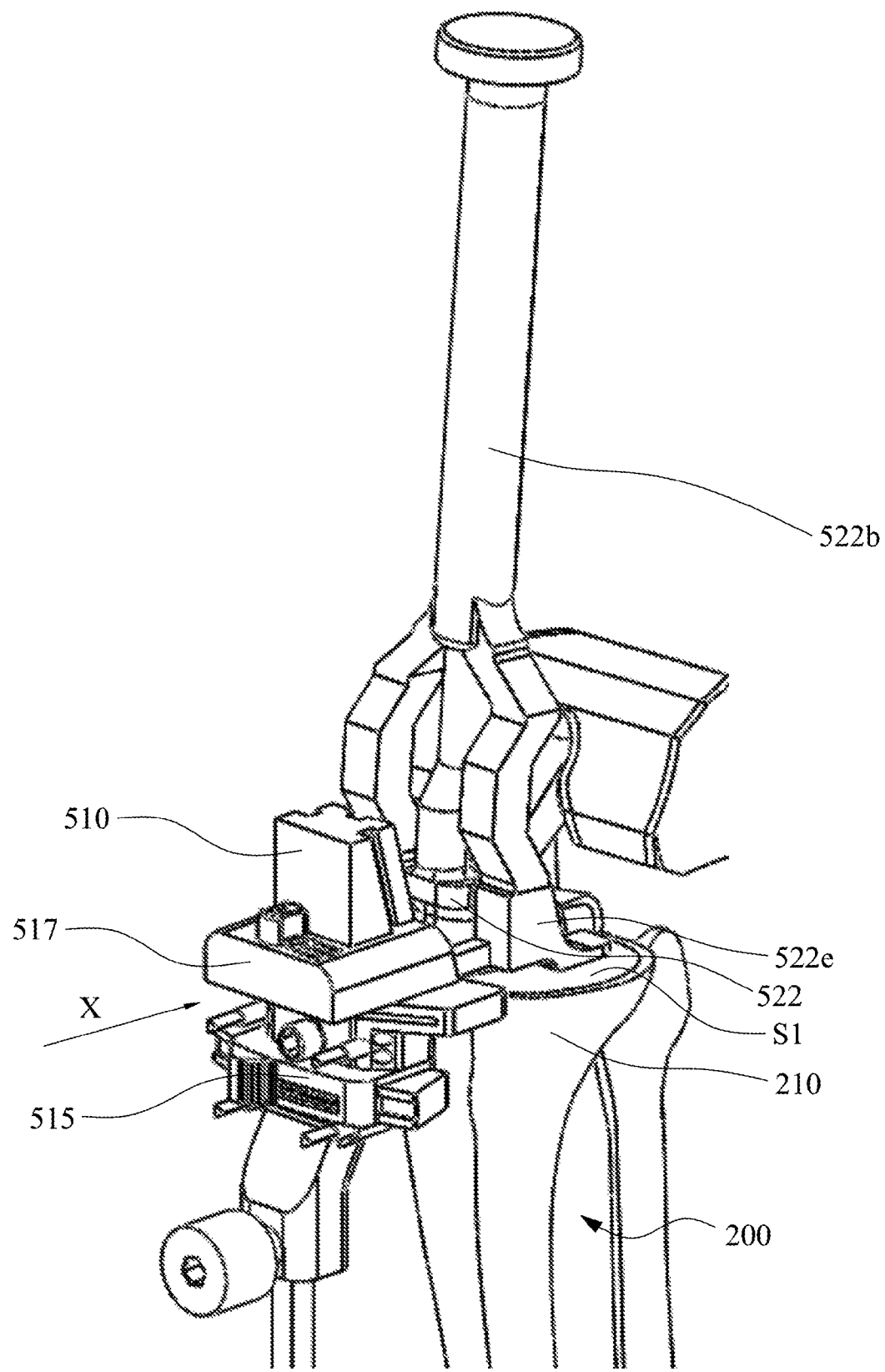
FIG. 35 is a perspective view showing the engagement of an internal punch to the tibia cut guide and the proximal end of the tibia.

FIG. 35 is a perspective view showing the engagement of an internal punch 522 to the tibia cut guide 510 and the proximal end 210 of the tibia 200. The internal punch 522 is used to finish the shaping of the tibial eminence 220 (blocked and not shown in FIG. 35) and is used for when the medial and lateral resection has already been made. As shown in FIG. 35, the internal punch 522 features a punch fixation base 522e that has adjustability in the anterior-posterior direction X. The punch fixation base 522e is only meant for the use of the internal punch 522. The AP length will be set to the measurement taken by the second VR guide. The punch fixation base 522e engages with the proximal end 210 of the tibia 200 to create a solid foundation for the internal punch 522. The internal punch 522 itself features a sheath 522b with features that engage with the punch fixation base 522e to correctly orient the internal punch 522. The surface of the punch fixation base 522e that engages with the internal punch 522 is at an angle with the resected surface S1. Within the sheath 522b there is a spring (blocked and not shown in FIG. 35) that will keep the internal punch 522 in an armed state that is ready to be impacted into the tibia 200.

Figure 36:
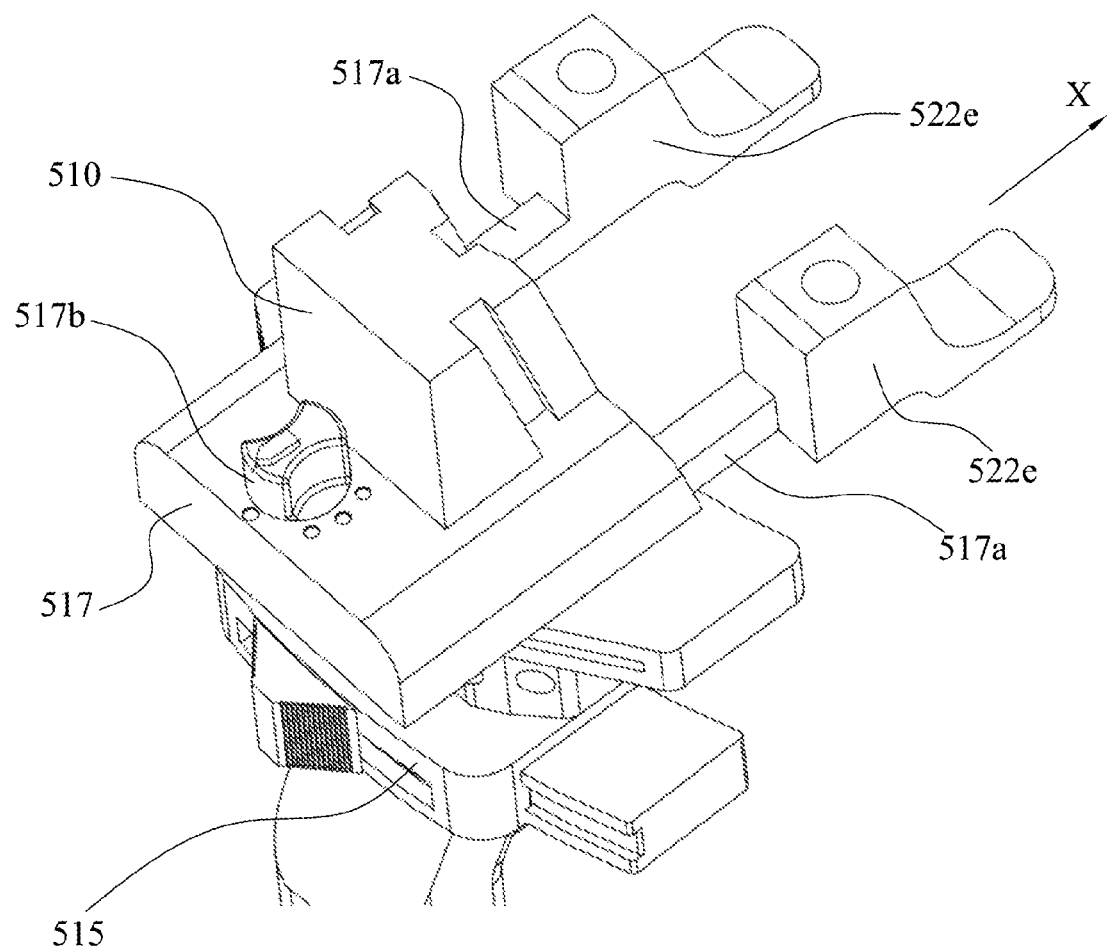
FIG. 36 is a perspective view of the anterior-posterior (AP) adjustment/calibration guide of FIG. 35.

To be more specific, as shown in FIG. 35, the anterior-posterior (AP) adjustment/calibration guide 517 is connected to the intermediate component 515. FIG. 36 is a perspective view of the anterior-posterior (AP) adjustment/calibration guide 517 of FIG. 35. Structurally speaking, as shown in FIG. 36, the AP adjustment/calibration guide 517 includes a pair of connection rods 517a and a turning knob 517b. Each of the connection rods 517a connects the punch fixation base 522e to the turning knob 517b in a way that the rotation of the turning knob 517b drives the movement of the connection rods 517a and thus the punch fixation bases 522e along the anterior-posterior direction X. In this way, the internal punch 522 relative to the tibia 200 can be calibrated in the anterior-posterior direction X.

In other words, the method for attaching the tibial base plate 100 on the tibia 200 further includes the following step:

(11) Calibrating the position of the internal punch 522 in the anterior-posterior (AP) direction X.

In practical applications, the second visual reference (VR) guide 860, the slot-pin mechanism 521a and the anterior-posterior (AP) adjustment/calibration guide 517 as mentioned above can work in conjunction with each other.

Figure 37:
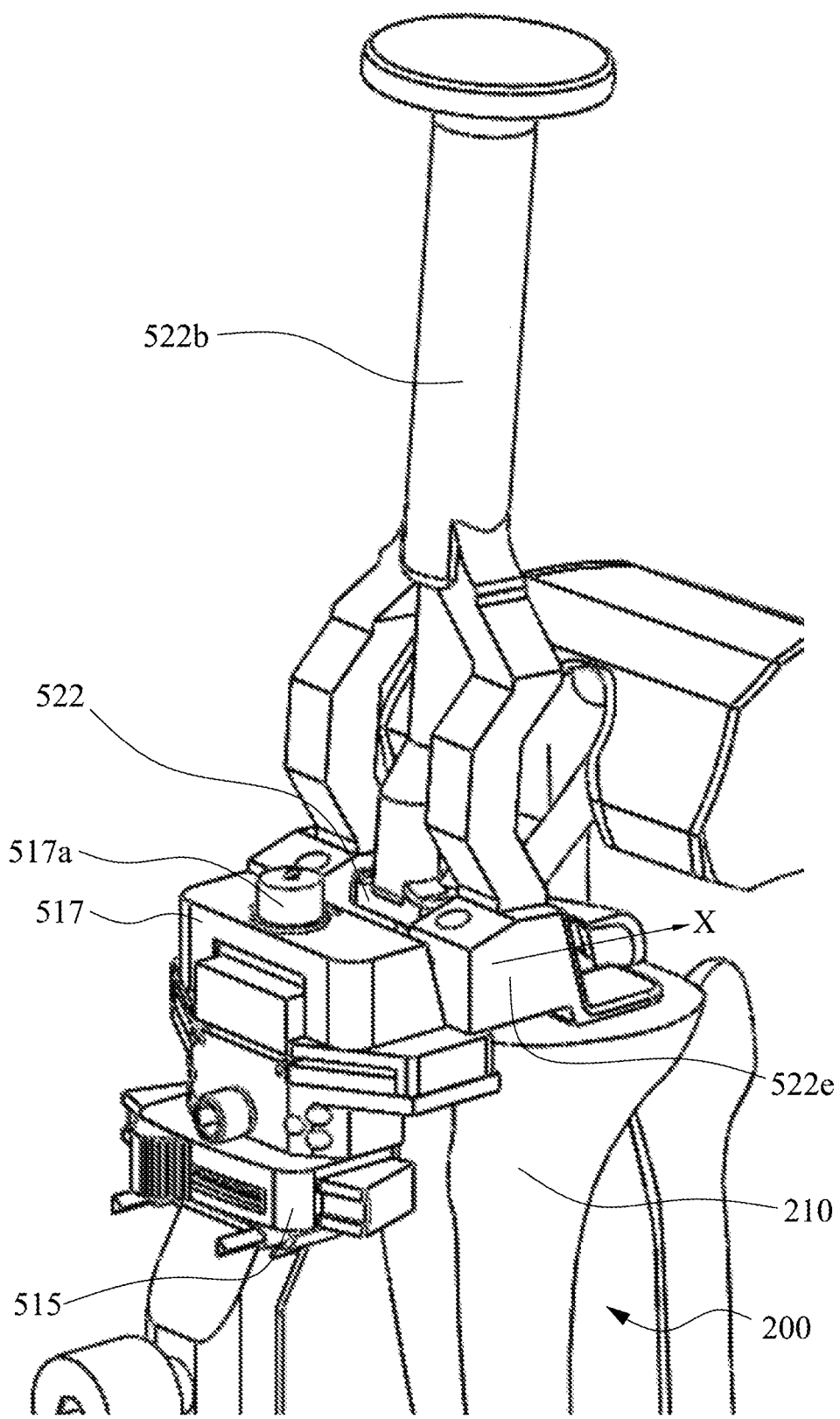
FIG. 37 is a perspective view showing the application of another internal punch.

FIG. 37 is a perspective view showing the application of another internal punch 522. As shown in FIG. 37, the internal punch 522 features a sheath 522b with pegs (blocked and not shown in FIG. 37) to engage with the punch fixation base 522e. Within the sheath 522b there is a spring (blocked and not shown in FIG. 37) to keep the internal punch 522 in an armed position for impacting. The sheath 522b and the punch fixation base 522e will properly position and orient the internal punch 522.

In summary, when compared with the prior art, the embodiments of the present disclosure mentioned above have at least the following advantages:

(1) In the embodiments of the present disclosure, the pair of the compartments of the tibial base plate forms a notch to accommodate the tibial eminence of the tibia. In this way, a bi-cruciate sparing orthopedic knee implant for the tibial portion of a total knee arthroplasty (TKA) procedure is allowed.

(2) In the embodiments of the present disclosure, the stem of the tibial base plate can be fitly engaged with the cutting slot on the resected surface into the proximal end of the tibia. In this way, the tibial base plate can be stably fixed to the resected surface.

(3) In the embodiments of the present disclosure, the bridge has a first contact surface sitting on the resected surface. In this way, the chance of anterior overhang is reduced.

(4) In the embodiments of the present disclosure, the inner surface of the tibial base plate flush with the notch is angled such that the notch diverges as insetting into the proximal end of the tibia. In this way, the tibial eminence is allowed to have a wider base and the chance of tibial avulsion is reduced.

Although the present disclosure has been described in considerable detail with reference to certain embodiments thereof, other embodiments are possible. Therefore, the spirit and scope of the appended claims should not be limited to the description of the embodiments contained herein.

It will be apparent to the person having ordinary skill in the art that various modifications and variations can be made to the structure of the present disclosure without departing from the scope or spirit of the present disclosure. In view of the foregoing, it is intended that the present disclosure cover modifications and variations of the present disclosure provided they fall within the scope of the following claims.

What is claimed is:

1. A tibial base plate configured for attachment to a resected surface at a proximal end of a tibia in a total knee arthroplasty (TKA) procedure, the tibial base plate comprising:
    a bridge having a first contact surface configured to sit on the resected surface;
    a first and a second compartments disposed at opposite sides of the bridge and extending in an anterior-posterior direction away from the bridge to form a notch configured to accommodate a tibial eminence of the tibia,
    wherein each of the first and the second compartments comprise a second contact surface configured to sit on the resected surface;
    wherein at least a portion of the bridge extends above a top surface of the first and the second compartments; and
    a stem connected to the bridge and the first and second compartments, the stem configured to be inset into the proximal end of the tibia,
    the stem having an outer surface facing away from the notch,
    wherein the outer surface is canted in the anterior-posterior direction towards the notch as insetting into the proximal end of the tibia,
    the stem configured to engage a cutting slot on the resected surface into the proximal end of the tibia, and
    wherein the tibial base plate comprises an inner surface flush with the notch and is at least partially located on the bridge, the compartments, and the stem,
    the inner surface is angled such that the notch diverges as insetting into the proximal end of the tibia,
    thereby allowing the tibial eminence to have a wider base in a direction of the tibial eminence extending towards the cutting slot.

2. The tibial base plate of claim 1, further comprising a pair of pegs respectively disposed on the second contact surfaces.

3. The tibial base plate of claim 2, wherein the pegs are canted and substantially parallel with the outer surface of the stem facing away from the notch.

4. The tibial base plate of claim 2 wherein each of the pegs is configured to engage a peg hole provided on the resected surface.

5. The tibial base plate of claim 1, wherein the compartments are symmetric.

6. The tibial base plate of claim 1, wherein the compartments are asymmetric.

7. The tibial base plate of claim 1 wherein the first compartment comprises a lip along an outer periphery of the first compartment, and the second compartment comprises a lip along an outer periphery of the second compartment.

8. The tibial base plate of claim 7 wherein the notch is defined by a distance between the lip of the first compartment and the lip of the second compartment.

9. The tibial base plate of claim 1 wherein the bridge has a similar width as at least a portion of the notch.

10. The tibial base plate of claim 9 wherein at least a portion of the notch has a width that is wider than the width of the bridge.

11. The tibial base plate of claim 1 wherein the bridge extends above the notch.

* * * * *